United States Patent [19]

Braughler et al.

[11] Patent Number: 4,948,533
[45] Date of Patent: Aug. 14, 1990

[54] 11A-HYDROXY STEROID DIESTER

[75] Inventors: John M. Braughler; Edward D. Hall, both of Portage; Wendell Wierenga; John M. McCall, both of Kalamazoo, all of Mich.

[73] Assignee: The Upjohn Company, Kalamazoo, Mich.

[21] Appl. No.: 312,337

[22] Filed: Feb. 16, 1989

Related U.S. Application Data

[63] Continuation of Ser. No. 912,677, Sep. 25, 1986, abandoned, which is a continuation of Ser. No. 701,601, Feb. 14, 1985, abandoned, which is a continuation-in-part of Ser. No. 594,096, Mar. 28, 1984, abandoned.

[51] Int. Cl.$^5$ .................... A61K 31/56; A61K 31/57; C07J 5/00
[52] U.S. Cl. .................... 552/576; 552/602; 552/566; 552/577; 552/575; 552/572; 552/595; 552/594; 514/179; 514/181; 540/111; 540/113; 540/114; 540/120; 540/88; 540/89; 540/10; 540/33
[58] Field of Search .................... 260/397.45, 397.47

[56] References Cited

U.S. PATENT DOCUMENTS

| | | | |
|---|---|---|---|
| 2,656,366 | 10/1953 | Minlon | 260/397.45 |
| 3,415,817 | 12/1968 | Philippson | 260/239.5 |
| 3,471,477 | 10/1969 | Fried | 260/239.5 |
| 3,546,215 | 12/1970 | Fried | 260/239.55 |
| 3,626,063 | 12/1971 | Lincoln et al. | 260/397.45 |
| 4,296,109 | 10/1981 | Laurent | 424/241 |

FOREIGN PATENT DOCUMENTS

| | | | |
|---|---|---|---|
| 2753838 | 7/1979 | Fed. Rep. of Germany | 260/397.45 |
| 1426922 | 2/1966 | France | 260/397.45 |
| 940701 | 10/1963 | United Kingdom | 260/397.45 |
| 1375357 | 11/1974 | United Kingdom | 260/397.45 |
| 1602266 | 11/1981 | United Kingdom | 260/397.45 |

OTHER PUBLICATIONS

Anderson, B. D., et al., "Influence of Premicellar and Micellar Association on the Reactivity of Methylprednisolone 21-Hemiesters in Aqueous Solution," J. Pharm. Sci. 72(4), Apr. 1983, pp. 448–454.

Anderson, B. D. and Taphouse, V., "Initial Rate Studies of Hydrolysis and Acyl Migration in Methyl Prednisolone 21-Hemisuccinate and 17-Hemisuccinate," J. Pharm. Sci. 70(2), Feb. 1981, pp. 181–186.

Flynn, G. L. and Lamb. D. J., "Factors Influencing Solvolysis of Corticosteroid-21-phosphate Esters," J. Pharm. Sci. 59(10), Oct. 1970, pp. 1433–1438.

Garrett, E. R., "Prediction of Stability in Pharmaceutical Preparations X: Alkaline Hydrolysis of Hydrocortisone Hemmisuccinate," J. Pharm. Sci. 51(5), May 1962, pp. 445–450.

Garrett, E. R., "The Solvolysis of 21-Hydrocortisone Esters and Hemiesters," J. Med. Pharm. Chem. 5, 1962, pp. 112–133.

Kawamura, M., et al., "Pharmaceutical Studies on Water-soluble Cortico-steroid Derivatives, III, Stability of Hydrocortisone-21-Sulfobenzoates and 21-Sulfate in Solution," Yakugaku Zasshi 91, 1971, pp. 871–878.

Kawamura, M., et al., "Pharmaceutical Studies on Water-soluble Cortico-steroid Derivatives, II, Stability of Hydrocortisone 21-Aminoalkylcarboxylates in Solution," Yakugaku Zasshi 91, 1971, pp. 863–870.

Yamamoto, R., et al., "Pharmaceutical Studies on Water-soluble Cortico-steroid Derivatives, I, Stability of Hydrocortisone 21-Hemiesters in Solution," Yakugaku Zasshi 91, 1971, pp. 855–862.

*Primary Examiner*—Floyd D. Higel
*Attorney, Agent, or Firm*—Bruce Stein; Ruth H. Newtson

[57] ABSTRACT

The present invention relates to 21-(3-carboxy-1-oxopropoxy) -17α-hydroxy-11α-(3,3-dimethyl-1-oxobutoxy)pregna-1,4-diene-3,20 dione and pharmaceutically acceptable salts thereof which are useful steroid prodrugs.

2 Claims, No Drawings

11A-HYDROXY STEROID DIESTER

The present patent application is a continuation of U.S. patent application Ser. No. 912,877, filed Sept. 25, 1986 (not abandoned) which was a continuation of U.S. patent application Ser. No. 701,601, filed Feb. 14, 1985 (now abandoned) which was a continuation-in-part of U.S. patent application Ser. No. 594,096, filed Mar. 28, 1984 (now abandoned).

BACKGROUND OF THE INVENTION

Conventional corticosteroids, such as cortisone, hydrocortisone, prednisone, methylprednisolone, etc., are generally poorly water soluble and therefore not suited for intravenous administration. Several types of soluble C-21 derivatives of such steroids have been disclosed in the patent literature including dicarboxylic acid hemiesters, sulfobenzoates, sulfopropionates, sulfates, phosphates, and aminoalkanoyloxy derivatives. While solubilization can generally be attained quite readily using a variety of such pro-moieties, most of the aforementioned derivatives possess other disadvantages limiting their utility as water soluble prodrugs. The term "prodrug" denotes a derivative of an active drug which is converted after administration back to the active drug. The "pro-moiety" referred to in this application is the fragment attached to the steroid via an ester linkage and removed by ester hydrolysis in vivo. A major problem with many common derivatives is their solution instability. Dicarboxylic acid hemiesters of corticosteroids such as succinate esters, for example, are marketed commercially as lyophilized powders for reconstitution prior to injection due to their solution instability (see, for example, E. R. Garrett, J. Pharm. Sci., 51, 445 (1962) and J. Med. Pharm. Che. 5, 112 (1962); B. D. Anderson and V. Taphouse, J. Pharm. Sci., 70, (1981); R. Yamamoto, S. Fujisawa, and M. Kawamura, Yakugaku Zasshi, 91, 855 (1971); B. D. Anderson, et al., J. Pharm. Sci. 72, 448 (1983)). Corticosteroid 21-aminoalkyl carboxylate derivatives reported in the literature also undergo rapid hydrolysis in aqueous solution (M. Kawamura, R. Yamamoto, and S. Fujisawa, Yakugaku Zasshi, 91, 863 (1971)).

Certain derivatives which do appear to exhibit better solution stability suffer from other disadvantages. 21-sulfate esters, for example, may not be readily converted to the active parent drug in vivo as suggested by the fact that the 21-sulfate of hydrocortisone is inactive in mice (M. Kawamura, R. Yamamoto, and S. Fujisawa, Yakugaku Zasshi, 91, 871 (1971); meta-sulfobenzoate esters which have been reported as having improved solution stability (M. Kawamura, R. Yamamoto and S. Fujisawa, ibid, French Patent derwent No. 76199U)) are frequently not highly water soluble and thus may have limited utility as injectable prodrugs. Phosphate esters may in some cases possess the requisite solubility, solution stability, and bioconversion rates but exhibit other disadvantages. Several undesirable features of phosphate esters are apparent: (1) Phosphate esters are often difficult to purify and are frequently very hygroscopic. (2). The stability of phosphate esters is optimum above pH 7 where other modes of drug degradation may be a problem. Glass surfaces are also more likely to delaminate in alkaline conditions resulting in particulate problems. (3) Precipitation of free corticosteroid due to the limited amount of hydrolysis which does occur may limit product shelf-life. Solubilization of free corticosteroid due to micelle formation by the intact prodrug is a desirable feature which phosphate esters exhibit to only a limited extent. (4) Concentrated solutions of phosphate esters of corticosteroids exhibit accelerated reaction velocities due to micelle formation, limiting shelf-life in concentrated solutions (G. L. Flynn and D. J. Lamb, J. Pharm. Sci. 59, 1433 (1970)). Sulfopropionate esters of corticosteroids have also been reported as readily water soluble and as having improved solution stability (Derwent Accession No. 27789 C). Sulfoacetate esters are also known (Derwent 9453F). The present invention provides a novel class of ester prodrugs of corticosteroids which do not possess the typical glucocorticoid activity.

FIELD OF INVENTION

The present invention is novel ester prodrugs of steroids and formulations thereof which have pharmacologically useful properties.

SUMMARY OF INVENTION

The compounds of the present invention are novel ester prodrugs of steroids which are solution stable in vitro but are rapidly converted in vivo to the active parent steroid and are therefore useful pharmacological agents. The compounds of the present invention are represented generically by general Formula I (see Formula Chart) wherein the various substituents have the following meanings:

the dotted line between positions C-1 and C-2 means the presence or absence of a second or double bond;

$R_1$ is $CH_3$ or $C_2H_5$;

$R_2$ is H and $R_3$ is in the α-position and is -OH, -O-alkyl($C_1$-$C_{12}$), —O—COalkyl($C_1$-$C_2$), -O-COaryl, -O-CON(R)$_2$, or OCOOR$_7$ wherein aryl is phenyl wherein f is 0 to 2 and wherein the phenyl ring is -(CH$_2$) optionally substituted with from 1 to 3 groups selected from Cl, F, Br, alkyl($C_1$-$C_3$), alkoxy($C_1$-$C_3$), thioalkoxy($C_1$-$C_3$), i.e., -S-alkyl($C_1$-$C_3$), Cl$_3$C-, F$_3$C, NH$_2$, and —NHCOCH$_3$, i.e., acetamido, or aryl is furyl, thienyl, pyrrolyl or pyridyl each of said hetero moiety being optionally substituted with one or two $C_1$-$C_4$ alkyl groups, and wherein R is hydrogen, alkyl($C_1$-$C_4$), or phenyl and each R can be the same or different; wherein $R_7$ is aryl as defined herein or alkyl($C_1$-$C_{12}$); or $R_2$ is α-Cl and $R_3$ is β-Cl; or $R_2$ and $R_3$ taken together form an oxygen (-O-) bridging positions C-9 and C-11; or $R_2$ and $R_3$ taken together form a second or a double bond between positions C-9 and C-11;

$R_4$ is H, $CH_3$, Cl or F;

$R_5$ is H, OH, F, Cl, Br, $CH_3$, phenyl, vinyl or allyl;

$R_6$ is H or $CH_3$;

$R_9$ is H, OH, $CH_3$, F or =$CH_2$;

$R_{10}$ is H, OH, $CH_3$ or $R_{10}$ forms a second or double bond between positions C-16 and C-17;

$R_{11}$ is —$CH_2CH_2COOH$. —Y—(CH$_2$)n—X—Y'—(CH$_2$)$_p$—X'—(CH$_2$)$_q$—NR$_{12}$R$_{13}$ or —Z(CH$_2$)$_r$Q, wherein Y is a bond or —O—; Y' is a bond, —O—, or —S—; each of X and X' is a bond, —CON(R$_{14}$)—, —N(R$_{14}$)CO—, —O—, —S—, —S(O)—, or —S(Oz)—; R$_{14}$ is hydrogen or alkyl($C_1$-$C_4$); each of R$_{12}$ and R$_{13}$ is a lower alkyl group of from 1 to 4 carbon atoms optionally substituted with one hydroxyl or R$_{12}$ and R$_{13}$ taken together with the nitrogen atom to which each is attached forms a monocyclic heterocyclic selected from pyrrolidino, piperidino, morpholino, thiomorpholino, piperazino or N(lower)alkylpiperazino wherein alkyl has from 1 to 4 carbon atoms; n is an integer of from 2 to 9; m is an integer of from 1 to 5; p is an integer of from 2 to 9; q is an integer of from 1 to 5; Z is a bond or —O—; r is an integer of from 4 to 9; and Q is (1) —$R_{15}$—$CH_2COOH$ wherein $R_{15}$ is —S—, —S(O)$_2$—, —S(O))$_2$—, —$SO_2 2N$—($R_{16}$)—, or —N($R_{16}$)$SO_2$—; $R_{16}$ is hydrogen or lower alkyl($C_1$–$C_4$); with the proviso that the number of carbon atoms in $R_{16}$ and $(CH_2)_r$ is not greater than 10;

(2) —CO—COOH; or (3) —C—N($R_{17}$)CH($R_{18}$)COOH wherein $R_{17}$ is H and $R_{18}$ is H, $CH_3$, —$CH_2COOH$, —$CH_2CH_2COOH$, —$CH_2OH$, —$CH_2SH$, —$CH_2CH_2SCH_3$, or —$CH_2Ph$—OH wherein Ph is phenyl and Ph—OH is p-hydroxyphenyl; or $R_{17}$ is $CH_3$ and $R_{18}$ is H; or $R_{17}$ and $R_{18}$ taken together are —$CH_2CH_2CH_2$—; or —N($R_{17}$)CH— ($R_{18}$)COOH taken together is —$NHCH_2CONHCH_2COOH$; and pharmaceutically acceptable salts thereof; with the further provisos that:

(a) when n is 2, $R_{14}$ is other than hydrogen;
(b) the sum of m and n is not greater than 10;
(c) the sum of p and q is not greater than 10;
(d) when X is a bond the sum of m and n is from 5 to 10;
(e) when X' is a bond the sum of p and q is from 4 to 9;
(f) when $R_4$ is Cl or F, the C-1 position is saturated; and
(g) when $R_9$ is =$CH_2$, $R_{10}$ is other than a second bond between positions C-16 and C-17; and with the overall proviso that the following compounds are excluded from the scope of this invention:

21-(3-Carboxy-1-oxopropoxy)-6α-fluoro-17α-hydroxy-16α-methylpregna-1,3,9(11)triene-3,20-dione, sodium salt;

21-(3-carboxy-1-oxopropoxy)-17α-hydroxy-16β-methylpregna-1,4,9-(11)triene-3,20-dione;

21-(3-carboxy-1-oxopropoxy)-17α-hydroxy-16β-methylpregna-1,4,9-(11)triene-3,20-dione, sodium salt;

21-(3-carboxy-1-oxopropoxy)-17α-hydroxy-16β-methylpregna-4,9(11)diene-3,20-dione, sodium salt;

N-methyltaurine amide of 17α-hydroxypregna-4,9(11)diene-3,20-dione-21-hemisuberate, sodium salt;

N-methyltaurine amide of 17α-hydroxypregna-1,4,9(11)triene-6α-fluoro-3,20-dione-21-hemisuberate, sodium salt.

Included within the scope of the present invention are pharmacologically acceptable salts of the compounds of Formula I. Solution stable formulations of the compounds of Formula I are also a part of the present invention.

DETAILED DESCRIPTION OF INVENTION

Preferred embodiments of the present invention are set forth in Formulas II to VI wherein the substituent groups have the following meanings:

In Formulas II to VI each of $R_4$, $R_7$ and $R_3$ is hydrogen; $R_1$ is alkyl($C_1$–$C_3$), preferably $CH_3$ or $C_2H_5$; $R_5$ is $CH_3$, F, Cl, Br, H or OH, and more preferably $R_5$ is in the α-position and is $CH_3$, H or F; $R_6$ is H or $CH_3$ and more preferably is H; $R_9$ is H, α-OH or $CH_3$; and $R_{10}$ is α-H or α-OH; and $R_{11}$ has the meaning defined in Formula I. Additionally in Formula III $R_2$ is hydrogen and $R_3$ is in the α-position and is OH, —O—alkyl($C_1$–$C_{12}$), preferably —O—alkyl($C_1$–$C_4$), —O—COalkyl($C_1$–$C_{12}$), preferably —O—COalkyl($C_1$–$C_6$), —O—COaryl, —O—CON(R)$_2$ or —OCOOR$_7$ wherein aryl, R, and $R_7$ have the meanings defined in Formula I and preferably aryl is phenyl and R is hydrogen or methyl.

Pharmacologically acceptable salts of the compounds of Formula I include acid addition salts and quaternary ammonium salts when $R_{11}$ is Y'—$(CH_2)_p$—X'—$(CH_2)_q$—$NR_{12}R_{13}$. Illustrative examples of such acid addition salts are inorganic salts such as hydrochloride, hydrobromide, sulfate, or phosphate, or organic salts such as acetate, malonate, succinate or sulfonates. Quaternary ammonium salts of compounds of Formula I containing a terminal amine group may be depicted as follows where $R_{11}$ is

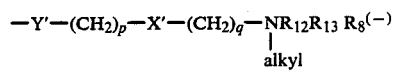

wherein Y', p, X', q, $R_{12}$ and $R_{13}$ have the meanings defined in Formula I, alkyl has from 1 to 4 carbon atoms, and $R_8^{(-)}$ represents an anion, for example $R_8$ is I, Br, Cl, $CH_3SO_3$ or $CH_3COO$.

To form acid addition salts of the compounds of Formula I containing a terminal amine function, said compounds are treated with suitable pharmaceutically acceptable inorganic or organic acids by standard procedures. Suitable inorganic acids are, for example, hydrochloric, hydrobromic, nitric, sulfuric or phosphoric acids. Suitable organic acids include carboxylic acids, such as, acetic, propionic, glycolic, lactic, pyruvic, malonic, succinic, fumaric, malic, tartaric, citric, stearic, ascorbic, maleic, hydroxymaleic, benzoic, hydroxybenzoic, phenylacetic, glutamic, glutaric, cinnamic, salicylic, 2-phenoxybenzoic or sulfonic acids such as methane sulfonic, sulfonilic, toluenesulfonic, or 2-hydroxyethanesulfonic. The quaternary ammonium salts are formed by contacting said compounds with a suitable akylating agent such as dimethyl sulfate, diethyl sulfate, or a suitable alkyl halide such as methyl or ethyl chloride or methyl or ethyl bromide or methyl or ethyl iodide.

Also included within the scope of this invention are base addition salts of compounds of Formula I wherein $R_{11}$ is —$CH_2CH_2COOH$, —Y—$(CH_2)_n$—X—$(CH_2)_m SO_3H$ or —Z$(CH_2)_r$Q which are obtained by treating the acid of Formula I with pharmaceutically acceptable inorganic or organic bases by standard procedures. Suitable inorganic bases are, e.g., those of alkali metal hydroxides, such as potassium, sodium, magnesium, and aluminum. Suitable organic bases are physiologically acceptable compounds containing tertiary amine functional groups, e.g., choline($OH^-$), trishydroxymethylmethylamine, triethanolamine, or trialkylamines such as triethylamine.

The aryl moiety in the $R_3$ group -OCOaryl is attached to the carbonyloxy moiety through any of the available ring carbon atoms of said aryl moiety.

Any reference herein to compounds of Formula I includes pharmacologically acceptable salts thereof.

The compounds of the present invention are useful in treating the following diseases and injuries: head trauma, spinal trauma, septic or traumatic shock, stroke, and hemorrhagic shock. In addition utility in cancer as well as other disorders or physiological phenomenon dependent on angiogenesis such as embryo implantation (antifertility), arthritis, and atherosclerosis is exhibited with these compounds coadministered with oral heparin or systemic heparin fragments (see J. Folkman, et al., Science 32, 719-725 (1983). The compounds of the present invention possess substantially none of the typical glucocorticoid effects.

The compounds of the present invention can be administered orally, intramuscularly, intravenously and by suppository, and the effective dosage range is 60 to 100 mg/kg/day. Additionally, a dosage regimen of using a loading dose of about 30 mg/kg followed by a repetitive as needed maintenance dose of about 15 mg/kg may be desirable. The compounds of the present invention may be coadministered with low doses of glucocorticoids. For the treatment of cancer including head tumors and other conditions dependent upon angiogenesis a preferred dosage range is 10 to 100 mg/kg/day and the preferred route of administration is orally, by suppository or intramuscularly.

The utility of the compounds of the present invention can be demonstrated in various test models as follows: For head trauma, mice are struck upon the head with a standard weight which is dropped from a set height. They are then dosed subcutaneously with the test compound. After one hour the motor abilities of the mice are assessed. Active test compounds promote improved motor activity relative to controls. For spinal trauma, see E. D. Hall and J. M. Braughler, Surg. Neurol. 18, 320-327 (1982) and J. Neurosurg. 56, 838-844 (1982). Septic (traumatic) shock is demonstrated in a rat whereby test compound is administered and protection of the rats from the lethal effects of endotoxin is measured. For stroke, the carotid arteries of gerbils are ligated for a brief period after which test compound is administered subcutaneously. The behavior of the gerbils is observed after a recovery period, and gerbils receiving test compound display a more normal behavior after the recovery period. And for hemorrhagic shock, by published procedures used to evaluate glucocorticoids.

The novel compounds of the present invention provide marked advantages over known steroids in that these novel compounds are highly water soluble which facilitates formulation of the compounds and permits long term storage of solutions of said novel compounds.

The solution stability of these compounds is due to several features: (1) The derivatives are highly soluble in the pH range 3 to 6 which is the pH range in which ester hydrolysis in aqueous solution is minimized. (2) Functional groups which may promote ester hydrolysis through any catalytic or substituent effect are sufficiently distant from the ester linkage that such influences are minimized. (3) The compounds self-associate in concentrated solutions to form molecular aggregates which increase the shelf life of formulations by (a) retarding hydroxide ion catalyzed ester hydrolysis at high concentrations, and (b) solubilizing any parent steroid present in and resulting from the hydrolysis of a solution of a compound of the present invention.

For storage of aqueous solutions of the compounds of Formula I the pH of their solution must be properly controlled. Ideally, the pH will be maintained at a level where the hydrolysis of the ester is at a minimum. This minimum depends to a certain degree on the chemical structure of the pro-moiety, the formulation concentration, and the temperature of storage but in general will be at a pH of about 3 to 6 for the compounds of this invention. A pH of 4 to 5 is preferred for compounds wherein $R_{11}$ is —$CH_2CH_2COOH$. Most advantageously, buffers should be employed to maintain the pH at or near the desired level throughout the shelf life of the formulation. Suitable buffers are those which are physiologically acceptable and exhibit sufficient buffer capacity in the pH range 3-6, e.g., acetate, citrate, succinate, or phthalate buffers and the like. The quantity of buffer used is determined by means known in the art and will depend on the pH desired, the concentration of the solution, and the buffering capacity of the buffer.

The concentration of the solution stable formulations of the compounds of Formula I depends on the activity level of and the ultimate dose of parent steroid desired. In general the stability of the formulations increases as the concentration of novel ester increases. In essence the solution stable formulations may be as concentrated as viscosity properties permit or until the solubility of the novel ester is exceeded.

Sterile aqueous solutions of the compounds of Formula I typically will contain other components such as preservatives, anti-oxidants, chelating agents, or other stabilizers. Suitable preservatives can include benzyl alcohol, the parabens, benzalkonium chloride, or benzoic acid. Anti-oxidants such as sodium bisulfite, ascorbic acid, propyl 3,4,5-trihydroxy benzoate, and the like may be employed. Chelating agents such as citrate, tartrate, or ethylenediaminetetraacetic acid (EDTA) may be used. Other additives useful as stabilizers of corticosteroid prodrugs (e.g., creatinine, polysorbate 80, and the like) may be employed.

Sterile aqueous solutions of compounds of Formula I can be administered to the patient being treated, i.e., a warm blooded mammal, intramuscularly or intravenously or orally. Additionally conventional solid dosage forms of the compounds of Formula I can be administered orally to the patient being treated. For example, capsules, pills, tablets or powders of the compounds of Formula I can be formulated in unit dosage forms incorporating conventional fillers, dispersants, preservatives and lubricants. Also suppositories providing a sustained release of a compound of Formula I can be formulated using conventional inert materials such as biodegradable polymers or synthetic silicones.

The compounds of the present invention are prepared by various routes using conventional procedures. For convenience in describing the preparation of the compounds of Formula I the symbol St is employed to represent that portion of Formula I as depicted by Formula VII.

PREPARATION OF COMPOUNDS OF FORMULA I

WHEREIN $R_{11}$ IS —Y—$(CH_2)_n$—X—$(CH_2)_m SO_3 H$

When Y is oxy, i.e., —O—, equimolar amounts of an intermediate of the formula $O_2N(C_6H_4)$—OCOO—$(CH_2)_n$—X—$C(CH_2)_m SO_3 H$ (Formula VIII) wherein ($C_6H_4$) is 1,4-phenylene and n, m, and X have the meanings defined in Formula I, and a parent steroid of the formula StOH wherein St has the meaning defined in Formula VII are reacted in a dry aprotic solvent such as tetrahydrofuran (THF), dimethylformamide (DMF) or dimethylsulfoxide (DMSO), in the presence of an acylation catalyst such as dimethylaminopyridine (DMAP) or N-methylimidazole. Although the reaction may be performed at room temperature it is convenient to gently warm the reaction mixture to about 50°-60° C. with stirring until all the activated carbonate ester is consumed. The product is purified by pouring the reaction mixture into water with the pH adjusted to ~4 and washing with an organic solvent, e.g., ether or ethyl acetate. It is then concentrated by removing the solvent and further purified either as the free acid or as an appropriate salt by crystallization and/or chromatography.

When Y is a bond equimolar amounts of an intermediate of the formula $HOOC(CH_2)_n$—$X$—$(CH_2)_m$—$SO_3H$ (Formula IX) wherein n, m, and X have the meanings defined in Formula I with a 21-iodo or 21-O-mesyl derivative of the parent steroid which may be represented respectively by the formulas St-Iodo (Formula X) and St-O-mesyl (Formula XI) wherein St has the meaning defined in Formula VII and mesyl means —S(O$_2$)—CH$_3$ are reacted. When the 21-iodo steroid derivative is employed the reaction proceeds at room temperature, whereas when the 21-O-mesyl steroid derivative is used the reaction is heated to about 60°-70° C. The reaction is carried out in a dry aprotic solvent such as DMF in the presence of a sterically hindered tertiary amine such as diisopropylethylamine. The product is isolated by diluting with water, adjusting the pH to ~5, washing with an organic solvent, suitably ethyl acetate, and further purifying by recrystallization or chromatography.

When Y is a bond and X is —CON(R$_{14}$)- compounds may also be prepared by reacting equimolar amounts of a 21-iodo steroid derivative of Formula XII and a bis-acid of the formula $HOOC$—$(CH_2)_n$—$COOH$ (Formula XII) wherein n has the meaning defined in Formula I in a dry aprotic solvent such as THF or DMF in the presence of a sterically hindered amine such as diisopropylethylamine with optional heating to give an intermediate of the formula $StOCO(CH_2)_n$—$COOH$ (Formula XIII) which is activated by cooling to about −20° to −10° C and reacting with isobutyl chloroformate in the presence of a tertiary amine, such as triethylamine for about 10-20 minutes during which time the reaction mixture is permitted to warm. To the activated derivative of Formula XIII is added an appropriate aminoalkylsulfonate of the formula

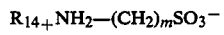
$R_{14+}NH_2$—$(CH_2)_mSO_3^-$             Formula XIV wherein m and R$_{14}$ have the meanings defined in Formula I. This latter reaction is complete within an hour, and the product is isolated by standard procedures, e.g., washing an aqueous solution, pH 5, with an appropriate organic solvent such as ethyl acetate, and purification by crystallization and/or chromatography.

Alternatively when Y is a bond and X is —CON(R$_{1-4}$)—to the above obtained activated derivative of Formula XIII is added p-nitrophenol in the presence of a tertiary amine such as triethylamine to give a stable intermediate of the formula $StOCO(CH_2)_nCOO$—$(C_6H_4)$—$NO_2$ (Formula XV) wherein St and n have the meanings defined in Formula I and (C$_6$H$_4$) is 1,4-phenylene. The intermediate of Formula XV is then reacted with a molar equivalent of an aminoalkylsulfonate of Formula XIV in a dipolar aprotic solvent such as THF or DMF in the presence of a base such as pyridine. The Formula I product is then isolated by washing an aqueous solution at pH 5 with an organic solvent, such as ethyl acetate, and purifying by crystallization and/or chromatography.

The compounds of Formula VIII wherein X is —CON(R$_{14}$)—are prepared by heating to about 60° C. a suitable aliphatic lactone, such as, propiolactone, γ-butyrolactone, δ-valerolactone, ε-caprolactone, etc., as n in Formula I increases in length, with an equimolar amount of an ω-aminoalkylsulfonate of Formula XIV in an aprotic solvent such as DMSO, DMF or THF to give the acyclic amide which is isolated by standard extractive procedures. The amide is reacted with p-nitrophenylchloroformate in a dry aprotic solvent such as THF in the presence of pyridine and isolated by standard procedures to give the compounds of Formula VIII or used without isolation to form compounds of Formula I.

The compounds of Formula VIII wherein X is —N(R$_{14}$)—CO—are prepared by reacting an appropriate ω-sulfo alkanoic acid having an alkylene chain length of from 1 to 5 carbon atoms with an ω-amino alcohol of the formula $HO$-$(CH_2)_n$—$NHR_{14}$, wherein n and R$_{14}$ have the meanings defined in Formula I, in a dry aprotic solvent, such as THF or DMF, in the presence of dicyclohexylcarbodiimide (DCC) to yield the amide. Any ester formed by reaction at the wrong end of the amino alcohol is eliminated by selective hydrolysis. Alternatively, a cyclic anhydride of Formula A (see Formula Chart) such as 3-sulfopropionic anhydride is reacted with an ω-amino alcohol in a polar aprotic solvent in the presence of a tertiary amine to form the amide. The product is isolated by standard extractive methods, and the product is taken up in a dry aprotic solvent and treated with p-nitrophenylchloroformate in the presence of pyridine to give the compounds of Formula VIII which may be isolated by standard procedures.

The compounds of Formula VIII wherein X is oxygen are prepared by reacting a suitable α,ω-aliphatic diol of the formula $HO(CH_2)_n$—$OH$ wherein n has the meaning defined in Formula I with an ω-halosulfonate of formula $Z'$-$(CH_2)_mSO_3$—where Z'=Cl, Br, I, —O—mesyl, or —O—tosyl and m is as defined in Formula I, or, alternatively, with a sultone of Formula B (see Formula Chart) wherein m is as defined in Formula I, in a dry aprotic solvent in the presence of one equivalent of potassium t-butoxide to yield the desired ether. This compound is purified by standard extractive methods, then is reacted with p-nitrophenyl chloroformate in a dry aprotic solvent in the presence of pyridine to give a reactive mixed p-nitrophenyl carbonate ester of Formula VIII.

To prepare the compounds of Formula VIII wherein X is sulfur, an aliphatic ω-halo alcohol of the formula $HO(CH_2)_n$-halo wherein n is as defined in Formula I and halo is chloro, bromo, or iodo is reacted with thiourea in refluxing lower alcohol to yield an isothiouronium salt which is then cleaved by treating the compound with an aqueous base to yield an ω-mercaptoalkanol $HS(CH_2)_nOH$—. The ω-mercapto alkanol, after isolation via standard methods, e.g., distillation, is then reacted with an ω-bromoalkylsulfonic acid of formula $Br(CH_2)_mSO_3H$ wherein m is as defined in Formula I or a sultone of Formula B in a solution containing two equivalents of inorganic base in water. A water miscible solvent (e.g., alcohol) may also be added to solubilize the reactants. The product of formula $HO(CH_2)_nS(CH_2)_mSO_3$—is isolated by standard extractive procedures. Final purification is achieved by recrystallization and/or chromatography. This product may be oxidized at this stage to give a sulfoxide or sulfone if desired, or it may be maintained in the sulfide form. To form the sulfoxide, i.e., X is —S(O)—, the sulfide is treated with one equivalent of sodium metaperiodate in aqueous lower alcohol at 0° C. When oxidation is complete the sodium iodate is filtered out and the sulfoxide isolated by standard procedures. To form the sulfone, i.e., X is —S(O$_2$)—, the sulfide is reacted with 30% H$_2$O$_2$ in 50% acetic acid at room temperature for several hours. Oxidation proceeds through the sulfoxide to the sulfone. The product is isolated by standard procedures, with final purification being achieved by recrystallization or by chromatography if needed. The sulfur-linked hydroxyl containing sulfonate is then converted to a reactive mixed carbonate ester by combining it with an equimolar quantity of p-nitrophenylchloroformate in an aprotic solvent with added pyridine to give the compounds of Formula VIII which may be isolated by standard procedures.

The compounds of Formula VIII wherein X is a bond are prepared by reacting a sulfoalkanol of the formula HO(CH$_2$)$_{n'}$SO$_3$H (Formula XVI) wherein n is from 5 to 10 with p-nitrophenylchloroformate in a dry polar aprotic solvent such as DMF or DMSO in the presence of a tertiary amine such as triethylamine. The reaction product is isolated by standard procedures to give a compound of Formula VIII or is used without isolation to prepare compounds of Formula I.

The compounds of Formula XVI may be prepared by reacting an alcohol of the formula HO—(CH$_2$)$_{n'}$—R$_b$ wherein n' has the meaning defined in Formula XVI and R$_b$ is Cl, Br, I, OS(O$_2$)CH$_3$ or OS(O$_2$)—(C$_6$H$_4$)—CH$_3$ with a sulfite salt such as sodium sulfite in a mixture of water and a water miscible alcohol such as ethanol or propanol. The reaction mixture is heated to reflux and when the desired product formation has taken place, the product may be isolated by standard extractive methods and/ or by crystallization.

Alternatively the compounds of Formula XVI may be synthesized in two steps involving the free radical addition of thioacetic acid to a compound of the formula HO-(CH$_2$)$_{n'-2}$—CH=CH$_2$ wherein n' has the meaning defined in Formula I, followed by oxidation of the resulting thiolacetate with hydrogen peroxide in acetic acid to form compounds of Formula XVI. The addition reaction is carried out in the presence of ultraviolet radiation or a peroxide catalyst such as dibenzoyl peroxide. The oxidation is carried out in acetic acid to which 90% hydrogen peroxide has been added and is heated to 65° to 70° C. The products are isolated by standard methods.

The compounds of Formula IX wherein X is a bond are prepared by reacting a bromoalkanoate of the formula Br—(CH$_2$)$_{n'}$—COO$^-$ wherein n' is from 5 to 10 with a molar excess of a sulfite salt in refluxing water or a mixture of water and a water miscible alcohol. The product may be isolated by crystallization or by standard extractive methods. Alternatively the compounds of Formula IX wherein X is a bond may be obtained in two steps by first reacting a terminal olefin of the formula CH$_2$=CH—(CH$_2$)$_{n'-2}$—COOH wherein n' is from 5 to 10 with thioacetic acid in the presence of ultraviolet radiation or a peroxide catalyst such as dibenzoyl peroxide under an inert atmosphere (e.g., N$_2$) to form a terminal thiolacetate of the formula CH$_2$—CO—S—(CH$_2$)$_{n'}$—COOH wherein n' is 5 to 10. The thiolacetate is isolated by standard methods and is then oxidized by treatment with hydrogen peroxide in acetic acid. The product of oxidation is a sulfoalkanoic acid of Formula IX which may be isolated by standard methods.

The compounds of Formula IX wherein X is —N(R$_{14}$)CO—are prepared by reacting an amino acid of the formula HN(R$_{14}$)(CH$_2$)$_n$—COOH with a bromoalkanoyl chloride wherein the alkanoyl moiety contains from 2 to 6 carbon atoms in an aqueous solvent at a pH of about 10 after which the pH is adjusted to about 3. The thus formed amide is extracted with an organic solvent such as ethyl acetate and isolated by procedures generally known in the art then taken up in aqueous alcohol and treated with sodium bisulfite to give the compounds of Formula IX which are isolated by standard procedures. Alternatively, the ω-amino acid may be reacted with a cyclic anhydride of Formula A (see Formula Chart) wherein m has the meaning defined in Formula I in an aprotic solvent or in aqueous media in the presence of a tertiary amine to yield the compounds of Formula IX.

The compounds of Formula IX wherein X is —CON(R$_{14}$)—are prepared by reacting an appropriate alkylene dicarboxylic acid with an appropriate aminoalkylsulfonate by procedures well known in the art.

The compounds of Formula IX wherein X is oxygen are prepared using t-butyl ester of a carboxylic acid of the formula

t-Bu-OCO(CH$_2$)n-halo wherein n is as defined in Formula I and halo is Cl, Br or I. This ester is prepared by reacting an appropriate ω-halo alkanoic acid of formula HOOC(CH$_2$)$_n$-halo with isobutylene gas in a dry aprotic solvent in the presence of catalytic amounts of sulfuric acid. The butyl ester is reacted with an ω-hydroxyalkyl sulfonic acid of formula HO(CH$_2$)$_m$SO$_3$H wherein m is as defined in Formula I in a dry aprotic solvent in the presence of a strong base such as potassium t-butoxide to yield an ether. The ether is isolated by standard methods well known in the art and the carboxylic acid is deprotected by treatment with trifluoroacetic acid. The compounds of Formula IX are isolated by removing trifluoroacetic acid and solvent under reduced pressure.

The compounds of Formula IX wherein X is sulfur are prepared by reaction of an ω-mercaptocarboxylic acid of the formula HOOC(CH$_2$)$_n$SH and an ω-bromoalkyl sulfonic acid of formula Br(CH$_2$)$_m$SO$_3$H or a sulfone of Formula B wherein n and m are as defined in Formula I in water containing three equivalents of inorganic base. A water miscible organic solvent, such as THF, may be added if required to solubilize the reactants. After several hours at 30°–50° C. the reaction is complete and the sulfide is isolated by extractive methods to give the compounds of Formula IX.

The compounds of Formula IX wherein X is sulfoxide are obtained by treating the corresponding Formula IX compound wherein X is sulfur with sodium periodate in water at 0° to 10° C. for ~10-20 hours. The aqueous solution is diluted with at least two volumes of acetonitrile, NaIO$_3$ precipitate is filtered out, and the product is isolated by standard methods. The compounds of Formula VIII wherein X is sulfone are obtained by treating the corresponding sulfur compound with 30% hydrogen peroxide in 50% acetic acid for several hours at room temperature. The product is again isolated by standard procedures.

The compounds of Formulas X and XI are prepared by general procedures well known in the art. The bis-acids of Formula XII and the aminoalkylsulfonates of Formula XIV are known in the art or are prepared by means well known in the art. Also, the other starting materials described hereinabove including the ω-halosulfonates, the compounds of Formula B, the ω-haloalcohols, the ω-amino acids, the compounds of Formula A, the ω-haloalkanoic acid esters, and the ω-hydroxyalkylsulfonic acids are commercially available, or are known in the art or prepared by procedures generally known in the art.

PREPARATION OF COMPOUNDS OF FORMULA I

WHEREIN $R_{11}$ IS $Y'$—$(CH_2)_p$—$X'$—$(CH_2)_q$—$NR_{12}R_{13}$ When $Y'$ is oxy, i.e., —O—, equimolar amounts of an amine of the formula $O_2N(C_6H_4)$—OCO)—$(CH_2)_p$—$X'$—$(CH_2)_q NR_{12}R_{13}$ (Formula XXIV) wherein $(C_6H_4)$ is 1,4-phenylene and p, q, $X'$, $R_{12}$ and $R_{13}$ have the meanings defined in Formula I, and a parent steroid of the formula StOH wherein St has the meaning defined in Formula VII are reacted in a dry aprotic solvent such as tetrahydrofuran (THF), dimethylformamide (DMF) or dimethylsulfoxide (DMSO), in the presence of an acylation catalyst such as dimethylaminopyridine (DMAP) or N-methylimidazole. Although the reaction may be performed at room temperature it is convenient to gently warm the reaction mixture to about 50°–60° C. with stirring until all the activated carbonate ester is consumed. The product is isolated by pouring the reaction mixture into water with the pH adjusted to 2–4, washing with an organic solvent, e.g., ether or ethyl acetate, then quickly adjusting the pH to 7–8 and extracting with an organic solvent such as ethyl acetate. The product is isolated by removing the solvent and purified by recrystallization or chromatographic techniques.

When $Y'$ is sulfur, i.e., —S—, equimolar quantities of an appropriate thiol amine of the formula $HS(CH_2)_p$—$X'$—$(CH_2)_q$—$NR_{12}R_{13}$ (Formula XVII) wherein p, q, $X'$, $R_{12}$ and $R_{13}$ have the meanings defined in Formula I, and a chloroformate derivative of the parent steroid represented by the formula StOCOCl (Formula XVIII) wherein St has the meaning defined in Formula VII with an equivalent quantity of a tertiary amine, such as triethylamine, are reacted in a dry aprotic solvent such as, THF, DMF or DMSO. The reaction mixture may be warmed gently if desired. The product is isolated by extraction with an organic solvent such as ethyl acetate or hexane and purified by crystallization or chromatography.

When $Y'$ is a bond the compounds are prepared by reacting equimolar amounts of an amino acid of the formula $HOOC(CH_2)_p$—$X'$—$(CH_2)_q NR_{12}R_{13}$ (Formula XIX) wherein p, q, $X'$, $R_{12}$ and $R_{13}$ have meanings defined in Formula I with a 21-iodo or 21—O—mesyl derivative of the parent steroid which may be represented respectively by the formulas St-Iodo (Formula XX) and St-O-mesyl (Formula XXI) wherein St has the meaning defined in Formula VII and mesyl means —S-(O_2)—CH_3. When the 21-iodo steroid derivative is employed the reaction proceeds at room temperature, whereas when the 21-O-mesyl steroid derivative is used the reaction is heated. Preferably both reactions are heated to about 60°–70° C. The reaction is carried out in a dry aprotic solvent such as DMF in the presence of a sterically hindered tertiary amine such as diisopropylethylamine. The product is isolated by extraction with an organic solvent, suitably ethyl acetate, and purified by recrystallization or chromatography.

When $Y'$ is a bond and X is —$CON(R_{14})$— the compounds may also be prepared by reacting equimolar amounts of a 21-iodo steroid derivative of Formula XX and a bis-acid of the formula $HOOC$—$(CH_2)_p$—$COOH$ (Formula XXIa) wherein p has the meaning defined in Formula I in a dry aprotic solvent such as THF or DMF in the presence of a sterically hindered amine such as diisopropylethylamine with optional heating to give an intermediate of the formula $St$—$OOC$—$(CH_2)_p$—$COOH$ (Formula XXII) which is activated by cooling to about −20° to −10° C. and reacting with isobutyl chloroformate in the presence of a tertiary amine, such as triethylamine for about 10-20 minutes during which time the reaction mixture is permitted to warm. To the activated derivative of Formula XXII is added an appropriate diamine of the formula $R_{14}NH$—$(CH_2)_q NR_{12}R_{13}$ (Formula XXV) wherein q, $R_{12}$, $R_{13}$, and $R_{14}$ have the meanings defined in Formula I. This latter reaction is complete within an hour, and the product is isolated by standard procedures, e.g., extraction with an appropriate organic solvent, such as ethyl acetate and purified by crystallization and/or chromatography.

Alternatively when Y is a bond and X is —$CON(R_{14})$—, to the above obtained activated derivative of Formula XXII is added p-nitrophenol in the presence of a tertiary amine such as triethylamine to give a stabile intermediate of the formula $StOOC(CH_2)_p$—$COO(C_6H_4)$—$NO_2$ (Formula XXIII) wherein St has the meaning defined in Formula VII, and $(C_6H_4)$ is 1,4-phenylene and p has the meaning defined in Formula I. The intermediate of Formula XXIII is then reacted with a molar equivalent of an amine of Formula XXV in a dipolar aprotic solvent such as THF or DMF in the presence of a base such as pyridine. The Formula I product is then isolated by extraction with an organic solvent, such as, ethyl acetate and purified by crystallization and/or chromatography.

The compounds of Formula XXIV wherein $X'$ is —$CON(R_{14})$—are prepared by heating to about 60° C. a suitable aliphatic lactone, such as, propiolactone, γ-butyrolactone, δ-valerolactone, ε-caprolactone, etc., as q in Formula XXV increases in length, with an equimolar amount of an aliphatic diamine of Formula XXV in an aprotic solvent such as DMSO, DMF or THF to give the acyclic amide which is isolated by diluting the reaction mixture with acidified water, washing with an immiscible solvent, such as ethyl acetate and adjusting the pH to about 12. The product is extracted with an organic solvent such as ethyl acetate, and the solvent is removed under reduced pressure to give the amide. The amide is reacted with p-nitrophenylchloroformate in a dry aprotic solvent such as THF in the presence of pyridine and isolated by standard procedures to give the compounds of Formula XXIV or used without isolation to form compounds of Formula I.

The compounds of Formula XXIV wherein $X'$ is —$N(R_{14})$—$CO$—are prepared by reacting an appropriate N,N dialkyl amino alkanoic acid having an alkylene chain length of from 1 to 5 carbon atoms with a chloroformate ester, such as isobutyl chloroformate, in a dry chilled aprotic solvent, such as THF or DMF, in the presence of a tertiary amine to give the carboxylate-activated amino acid. This solution is then added dropwise with stirring to a second solution containing an equimolar amount of an amino alcohol of the formula HO—(CH$_2$)$_p$—NH(R$_{14}$) wherein p and R$_{14}$ have the meanings defined in Formula I. An amide is obtained and any ester formed by reaction at the wrong end of the amino alcohol is eliminated by selective hydrolysis. The product is isolated by standard extractive methods, and the oily product is taken up in a dry aprotic solvent and treated with p-nitrophenylchloroformate in the presence of pyridine to give the compounds of Formula XXIV which may be isolated by standard procedures.

The compounds of Formula XXIV wherein X' is oxygen are prepared by reacting a suitable hydroxyalkoxyalkyl halide of the formula HO—(CH$_2$)$_n$—O(CH$_2$)$_q$—halide wherein p and q have the meanings defined in Formula I and halide is, e.g., chloride or bromide with an amine of the formula HNR$_{12}$R$_{13}$ wherein R$_{12}$ and R$_{13}$ are as defined in Formula I in a dry aprotic solvent with a catalytic amount of NaI present to yield an amino alcohol. After purifying the amino alcohol by extractive methods, it is taken up in a dry aprotic solvent and reacted with p-nitrophenylchloroformate in the presence of pyridine to give a reactive mixed p-nitrophenyl carbonate ester of Formula XXIV.

To prepare the compounds of Formula XXIV wherein X' is sulfur, an aliphatic ω-halo alcohol of the formula HO(CH$_2$)$_p$ halo wherein p is as defined in Formula I and halo is chloro or is reacted with an aliphatic thiol of the formula HS(CH$_2$)$_q$NR$_{12}$R$_{13}$ wherein q, R$_{12}$ and R$_{13}$ are as defined in Formula I, to give a sulfide. The reaction is carried out in a partially aqueous solvent with a slight excess of NaOH and a reducing agent, e.g., sodium bisulfite, to inhibit disulfide formation. The product is isolated by extractive methods. This product may be oxidized at this stage to give a sulfoxide or sulfone if desired, or it may be maintained in the sulfide form. To form the sulfoxide, i.e., X' is —S(O)—, the sulfide amino alcohol is treated with one equivalent of sodium metaperiodate in aqueous lower alcohol at 0° C. When oxidation is complete the sodium iodate is filtered out and the sulfoxide isolated by standard procedures. To form the sulfone, i.e., X is —S(O$_2$)—, the sulfide amino alcohol is dissolved in a large excess of 90% formic acid and heated to about 70° C. for several minutes. After cooling to room temperature the solution is treated with 30% hydrogen peroxide. Oxidation proceeds through the sulfoxide to the sulfone. When the oxidation is complete, most of the formic acid is removed under reduced pressure, and the remaining residue is taken up in methanolic HCl. After one hour the mixture is concentrated under reduced pressure to give the desired sulfone-linked amino alcohol as the HCl salt. Final purification is achieved by recrystallization or by chromatography if needed. The sulfur-linked amino alcohol is then converted to a reactive mixed carbonate ester by combining it with an equimolar quantity of p-nitrophenylchloroformate in an aprotic solvent with added pyridine to give the compounds of Formula XXIV which may be isolated by standard procedures.

The compounds of Formula XXIV wherein X' is a bond are prepared by reacting an amino alkanol of the formula HO(CH$_2$)$_p$—NR$_{12}$R$_{13}$ wherein p, R$_{12}$ and R$_{13}$ are as defined in Formula I with p-nitrophenylchloroformate in a dry aprotic solvent, such as, THF in the presence of an amine, such as, triethylamine. The amino alkanol compounds are known in the art or are prepared by generally known procedures by treatment of an appropriate ω-iodoalkanol with an amine of the formula NHR$_{12}$R$_{13}$ wherein R$_{12}$ and R$_{13}$ are as defined in Formula I.

The compounds of Formula XVII wherein X' is a bond are prepared by reacting equimolar amounts of an ω-haloalkylamine of the formula halo—(CH$_2$)$_p$—NR$_{12}$R$_{13}$ wherein halo is halogen and p, R$_{12}$ and R$_{13}$ are as defined in Formula I and thiourea in propylene glycol at an elevated temperature. When the halide has been displaced, the isothiouronium salt is cleaved by adding an amine such as tetraethylene pentamine and continuing to apply heat. When the free thiol has formed, this product is isolated by extractive means or by distillation under reduced pressure.

The compounds of Formula XIX wherein X' is a bond are known in the art or are prepared by procedures well known in the art.

To prepare the compounds of Formula XVII wherein X' is —CON— (R$_{14}$)-an ω-haloalkylC$_{2-9}$- carboxylic acid is reacted with equimolar quantitities of triethylamine and isobutylchloroformate at −10° C. in an aprotic solvent, preferably THF. The solution is allowed to warm to room temperature and a diamine of the formula NH(R$_{14}$)(CH$_2$)$_q$NR$_{12}$R$_{13}$ wherein R$_{14}$, R$_{12}$, R$_{13}$ and q have the meanings defined in Formula I is added. After about 30 minutes the amide product is isolated by extractive procedures. This product is then reacted with an equimolar amount of thiourea in propylene glycol at an elevated temperature. When the halide has been displaced, the isothiouronium salt is cleaved by adding an amine such as tetraethylene pentamine and continuing to apply heat. When the free thiol has formed, this product is isolated by extractive means or by distillation under reduced pressure.

To prepare compounds of Formula XVII wherein X' is —N(R$_{14}$)CO—an amino acid of the formula HOOC(CH$_2$)$_q$NR$_{12}$R$_{13}$ wherein q, R$_{12}$ and R$_{13}$ are as defined in Formula I is activated by reaction with isobutylchloroformate in a chilled dry aprotic solvent, such as THF, with sufficient triethylamine to take up the liberated HCl. This solution is allowed to warm to room temperature and is then added dropwise under nitrogen to a solution containing an amino alcohol of the formula HO(CH$_2$)$_p$NH—(R$_{14}$) wherein p and R$_{14}$ are as defined in Formula I. The amide thus obtained is purified by standard procedures. This amide is then dissolved in pyridine and is treated with methane sulfonyl chloride to give the terminal mesyl group. The pyridine is removed under reduced pressure, and the product is heated with a 10% molar excess of thiourea in propylene glycol. When the displacement of the mesyl group by thiourea is complete the resulting isothiouronium salt is cleaved by heating with added tetraethylenepentamine to give the compounds of Formula XVII which are isolated by extractive procedures or by distillation.

The compounds of Formula XVII wherein X' is oxygen are prepared by reacting an N,N-disubstitutedamino alcohol of the formula HO(CH$_2$)$_q$—NR$_{12}$R$_{13}$ wherein q. R$_{12}$ and R$_{13}$ are as defined in Formula I with an equimolar quantity of sodium hydride in DMF to form the sodium alkoxide. This solution is then added dropwise to a large molar excess of an aliphatic C$_{2-9}$ dihalide or a dimesylate in DMF. If the halogen groups are chloride, sodium iodide is added as a catalyst. When ether formation is complete, the desired mono ether is isolated by extractive procedures then treated with thiourea in refluxing 95% ethanol to yield the isothiouronium salt. This salt is cleaved by treating the solution with a slight molar excess of sodium hydroxide solution and continuing to reflux the mixture under nitrogen. The amino thiol is then isolated from the reaction mixture by extractive procedures to give the compounds of Formula XVII.

The compounds of Formula XVII wherein X' is sulfur are prepared as follows. An N,N-disubstitutedamino thiol of the formula $HS(CH_2)_q$—$NR_{12}R_{13}$ wherein q, $R_{12}$ and $R_{13}$ are as defined in Formula I is dissolved in a lower alcohol and treated with a slight molar excess of NaOH. This solution is then added dropwise to a large molar excess of a dibromide of the formula $Br(CH_2)_pBr$ wherein p is an integer from 2 to 9, in an aprotic solvent such as DMF or THF. The desired monosulfide is isolated by standard extractive procedures. At this stage, the sulfide could be oxidized, if desired, to give either the sulfoxide or the sulfone. To prepare the compounds of Formula XVII wherein X' is sulfoxide the sulfide obtained above is treated with sodium metaperiodate in a lower aqueous alcohol by procedures analogous to those described hereinabove in connection with the preparation of compounds of Formula XXIV. To prepare the compounds of Formula XVII wherein X' is sulfone the sulfide is dissolved in glacial acetic acid and treated with 30% hydrogen peroxide thus oxidizing the sulfide through the sulfoxide to the sulfone. Whether or not further oxidation is elected, the subsequent steps are the same. The sulfur-linked amino bromide is treated with an equimolar amount of thiourea in refluxing 95% ethanol to yield an isothiouronium salt. This salt is cleaved by the addition of concentrated base to yield the free thiol. Upon acidification and extractive workup the compounds of Formula XVII are obtained.

The steroid chloroformates of Formula XVIII are prepared by reacting the parent 21 hydroxy steroid with a molar excess of phosgene in THF in a chilled reaction vessel which is then allowed to warm to room temperature. After about one hour the solution is concentrated under reduced pressure and the chloroformate precipitates out.

The compounds of Formula XIX wherein X' is —$N(R_{14})CO$—are prepared by reacting an aminoacid of the formula $HN(R_{14})(CH_2)_p$—COOH with a ω-bromoalkanoyl chloride wherein the alkanoyl moiety contains from 2 to 6 carbon atoms in an aqueous solvent at a pH of about 10 after which the pH is adjusted to about 3. The thus formed amide is extracted with an organic solvent such as ethyl acetate and isolated by procedures generally known in the art then taken up in an aprotic solvent such as THF or DMF and treated with an amine of the formula $HNR_{12}R_{13}$ wherein $R_{12}$ and $R_{13}$ have the meanings defined in Formula I to give the compounds of Formula XIX which are isolated by standard procedures.

The compounds of Formula XIX wherein X' is —$CON(R_{14})$— are prepared by reacting an appropriate alkylene dicarboxylic acid with an appropriate alkylenediamine by procedures well known in the art.

The compounds of Formula XIX wherein X' is oxy are prepared as follows. A t-butyl ester of a carboxylic acid of the formula t-bu—$OCO(CH_2)_{p-1}$-$CH_2$-$R_b$ wherein p is as defined in Formula I and $R_b$ is a leaving group such as chloro, bromo, iodo, O-mesyl or O-tosyl is treated with an ω-hydroxy amine of the formula $HO(CH_2)_qNR_{12}R_{13}$ wherein q, $R_{12}$ and $R_{13}$ are as defined in Formula I, e.g., 2-diethylamino ethanol, and an equimolar amount of a strong non-nucleophilic base, e.g., potassium t-butoxide, in a dry aprotic solvent, e.g., THF, to yield the ether coupled promoiety. If the displaceable group is chloro or bromo, NaI may be added as a catalyst. When the ether formation is complete the product is isolated by extractive methods. The t-butyl ester is hydrolyzed by treatment with toluene sulfonic acid in an organic solvent, e.g., toluene, or with anhydrous trifluoroacetic acid to give the compounds of Formula XIX.

The compounds of Formula XIX wherein X' is sulfur are prepared by reaction of an ω-mercaptocarboxylic acid of the formula $HOOC(CH_2)_pSH$ and an ω-halo amine of the formula halo $(CH_2)_qNR_{12}R_3$ wherein p, q, $R_{12}$ and $R_{13}$ are as defined in Formula I and halo is chloro or bromo, in aqueous base containing a reducing agent, such as $K_2S_2O_5$. The pH is maintained at 10–12 by addition of base if necessary. A water miscible organic solvent, such as THF, may be added if required to solubilize the ω-halo-amine. When the reaction is complete the sulfide is isolated by extractive methods to give the compounds of Formula XIX.

The compounds of Formula XIX wherein X' is sulfur are obtained by treating the corresponding Formula XIX compound wherein X' is sulfur with sodium periodate in a lower aqueous alcohol as described hereinabove. The compounds of Formula XIX wherein X' is sulfone are obtained by treating the corresponding sulfur compound with hydrogen peroxide in 50% acetic acid by procedures analogous to those described hereinbefore.

The compounds of Formulas XX and XXI are prepared by general procedures well known in the art. The bis-acids of Formula XXIa and the alkylenediamines of Formula XXV are known in the art or are prepared by means well known in the art.

The ω-mercaptocarboxylic acids employed hereinabove are obtained by treating an acid of the formula $HOOC(CH_2)_pR_c$ wherein $R_c$ is chloro, bromo, iodo, O-mesyl or O-tosyl and p is 2 to 9 with thiourea in a refluxing lower alcohol to give the isothiouronium salt which is subsequently cleaved by addition of aqueous base under reducing conditions to give the free thiol group.

The ω-haloamines employed hereinabove wherein m is other than 2 are obtained by adding a secondary amine of the formula $HNR_{12}R_{13}$ wherein $R_{12}$ and $R_{13}$ are as defined in Formula I portionwise to a molar excess of an appropriate 1,ω-alkylenedihalide. Generally the reaction mixture is heated and if the halide is chloride, an iodide salt may be added as a catalyst. The ω-haloamines wherein q is 2 are commercially available.

PREPARATION OF COMPOUNDS OF FORMULA I WHEREIN $R_{11}$ IS $Z$-$(CH_2)_rQ$

When Z is a bond, Q is $R_{15}$-$CH_2COOH$ and $R_{15}$ is —S—, —S(O)— or —$S(O)_2$— the compounds are prepared by reacting a steroid of the formula St-$X_5$ (Formula XXVI) wherein St has the meaning defined in Formula VII and $X_5$ is —$OSO_2CH_3$ or iodo, with a molar excess of a compound of the formula $HOOC(CH_2)_r$—$R_{15}$—$CH_2COOH$ (Formula XXVII) wherein $R'_{15}$ is —S—, —S(O)—, or —$S(O)_2$— and r is an integer from 2 to 9. The reaction is carried out in a polar aprotic solvent such as DMF or DMSO in the presence of at least 2 moles of an appropriate base per mole of the compound of Formula XXVII. The most preferred base is a bicyclic amidine such as 1,8-diazabicyclo[5.4.0]undec-7-ene (DBU).

Compounds of Formula XXVII wherein $R'_{15}$ is —$SO_2$— are prepared by treating a compound of the formula $HOCO(CH_2)_rSCH_2$—COOH (Formula XXVIII) with a strong oxidant such as 1:1 mixture of glacial acetic acid and 30% hydrogen peroxide. Compounds of Formula XXVII wherein $R_{15}$ is —SO— are prepared by treating a compound of Formula XXVIII with an equimolar amount of sodium periodate ($NaIO_4$) in aqueous methanol at 0° to 10° C. for approximately one day. The reaction should be monitored to prevent over oxidation to the sulfone. Compounds of Formula XXVIII are prepared by reacting one equivalent of a compound of the formula $HOCO(CH_2)_rBr$ (Formula XXIX) with one equivalent of mercaptoacetic acid in water in the presence of three equivalents of strong base such as NaOH or KOH.

When Z is a bond, Q is $R_{15}$—$CH_2COOH$ and $R_{15}$ is —$N(R_{16})SO_2$— the compounds are prepared by treating a compound of the formula $HOOC—(CH_2)_rN(R_{16})SO_2CH_2COOH$ (Formula XXX) wherein r and $R_{16}$ are as defined in Formula I with one equivalent of a compound of Formula XXVI wherein $X_5$ is iodo, in a polar aprotic solvent such as dimethyl formamide, dimethyl sulfoxide or tetrahydrofuran in the presence of at least two equivalents of a bicyclic amidine such as 1,8-diazabicyclo[5.4.0]undec-7-ene or a sterically hindered tertiary amine such as diisopropylethylamine. Preferably the reaction is carried out at room temperature using two equivalents of DBU.

Compounds of Formula XXX are prepared by treating compounds of the formula $R_aOOC(CH_2)_rN(R_{16})SO_2CH_2COOR_a$ (Formula XXXI) with aqueous mineral acid.

In Formula XXXI r and $R_{16}$ are as defined in Formula I and $R_a$ is a lower alkyl($C_1$–$C_4$) straight or branched chain. Compounds of Formula XXXI are prepared by treating an amino acid ester of the formula $R_aOOC(CH_2)_rN(R_{16})H$ wherein $R_a$, r and $R_6$ are as defined in Formula XXXI with a sulfonyl chloride of the formula $ClSO_2CH_2COOR_a$ wherein $R_a$ is as defined in Formula XXXI in a polar aprotic solvent in the presence of pyridine as a catalyst. The amino ester compounds are prepared by refluxing an amino acid of the formula $HOOC(CH_2)_rN(R_{16})H$ wherein r and $R_{16}$ are as defined in Formula I in an appropriate lower alcohol in the presence of a catalytic amount of sulfuric acid or anhydrous hydrochloric acid. The amino acids are known in the art or are obtained by treating an acid of the formula $HOOC(CH_2)_rL$ wherein L is Cl, Br, I, O-mesyl or O-tosyl with an amine of the formula $R_{16}NH_2$. The sulfonyl chloride compounds are prepared by treating a sulfoacetic acid of the formula $HSO_3CH_2COOR_a$ wherein $R_a$ is as defined above with thionyl chloride in an aprotic solvent or neat with excess thionyl chloride. Dimethylformamide may be added as a catalyst. The sulfoacetic acids are prepared by esterification of sulfoacetic acid in a refluxing lower alcohol.

When Z is a bond, Q is $R_{15}$—$CH_2COOH$ and $R_{15}$ is —$SO_2N(R_{16})$— the compounds are prepared by condensing a bis-acid of the formula $HOOC(CH_2)_rSO_2N(R_{16})CH_2COOH$ (Formula XXXII) wherein r and $R_{16}$ are as defined in Formula I with a compound of Formula XXVI wherein $X_5$ is iodo in a polar aprotic solvent in the presence of at least two equivalents of DBU or a hindered tertiary amine per equivalent of compound of Formula XXXII. The compounds of Formula XXXII are prepared by acid or base hydrolysis of the corresponding bis ester, i.e., a compound of formula $R_aOOC(CH_2)_rSO_2N(R_{16})CH_2COOR_a$ wherein $R_{16}$, r and $R_a$ are as defined hereinabove, and the bis ester is obtained by condensing an amine ester of the formula $H(R_{16})NCH_2COOR_a$ with sulfonyl chloride of the formula $R_aOOC(CH_2)_rSO_2Cl$ in a polar aprotic solvent such as dimethyl formamide, tetrahydrofuran or dimethylsulfoxide in the presence of pyridine as a catalyst. The sulfonyl chloride is obtained by treating an acid of the formula $HOOC(CH_2)_rR_b$ wherein $R_b$ is, e.g., Cl, Br, I, O-mesyl or O-tosyl with sodium sulfite in aqueous methanol or ethanol at reflux to give the sulfonic acid $HOOC(CH_{2n}SO_3H$ which is further refluxed in an anhydrous lower alcohol to give the carboxy ester derivative which is treated with excess thionyl chloride in the presence of a catalytic amount of dimethyl formamide.

When Z is —O—, Q is $R_{15}CH_2COOH$ and $R_{15}$ is S, S(O) or $S(O)_2$, the compounds are prepared by reacting a steroid StOH wherein St is as defined in Formula VII with a compound of the formula $R_cOCOO(CH_2)_rR'_{15}$—$CH_2COOR_g$ (Formula XXXIII) wherein $R_c$ is p-nitrophenyl, $R'_{15}$ is S, S(O) or $S(O)_2$, and r is an integer of from 2 to 9, and $R_g$ is $CH_3$ or 2,2,2-trichloroethyl in a polar aprotic solvent such as tetrahydrofuran, dimethylformamide or 4-dimethylsulfoxide in the presence of an acylation catalyst such as dimethylaminopyridine (DMAP) or N-methylimidazole and subsequently acid hydrolyzing the resulting ester to the corresponding acid. The Formula XXXIII compounds are prepared by treating an alcohol of the formula $HO(CH_2)_r$—$R'_{15}$—$CH_2COOR_g$ wherein $R'_{15}$, r, and $R_g$ are as defined above with equimolar amounts of p-nitrophenyl chlorocarbonate and a tertiary amine, e.g., triethylamine or pyridine in an aprotic solvent such as acetone, chloroform or tetrahydrofuran. The alcohols wherein $R'_{15}$ is —S— are obtained by reacting one equivalent of a compound of the formula $HO(CH_2)_rR_b$ wherein r is 4 to 9 and $R_b$ is Cl, Br, I, O-mesyl or O-tosyl with one equivalent of mercapto-acetic acid in water in the presence of sodium hydroxide or potassium hydroxide. The thus obtained compounds of the formula $HO(CH_2)_r$—$S$—$CH_2COOH$ are esterified, e.g., by treatment with a catalytic amount of a strong acid such as, sulfuric acid or toluenesulfonic acid in methanol at reflux or by treatment with 2,2,2-trichloroethanol in the presence of a catalytic amount of a mineral acid at 65° to 95° C. Following esterification the sulfur compounds can be oxidized to the sulfone by treatment with an equimolar amount of $NaIO_4$ in an aqueous alcohol at 0° to 10° C. or to the sulfoxide by treatment with potassium hydrogen persulfate in aqueous alcohol. These oxidation steps may convert the carboxy methyl ester to the free acid and thus the resulting sulfone and sulfoxide can be reesterified as generally described above.

When Z is —O—, Q is $R_{15}$—$CH_2COOH$, and $R_{15}$ is —$SO_2N(R_6)$— the compounds are prepared by treating a compound of the formula $R_cOCOO(CH_2)_rSO_2N(R_{16})CH_2COOCH_3$ (Formula XXXIV) wherein $R_{16}$ and r are as defined in Formula I and $R_c$ is p-nitrophenyl with a corticosteroid of the formula StOH wherein St is as defined in Formula VII in a polar aprotic solvent such as dimethylformamide, tetrahydrofuran, or dimethylsulfoxide in the presence of one equivalent of a tertiary amine such as pyridine or triethylamine and a catalytic amount of an acylation catalyst such as 4-dimethylaminopyridine or N-methylimidazole and selectively hydrolyzing the resulting ester to the acid by treating the ester with an aqueous solution of a strong acid such as hydrochloric or sulfuric. The Formula XXXIV compounds are prepared by treating a sulfonyl chloride of the formula $R_cOCOO(CH_2)_rSO_2Cl$ wherein r and $R_c$ are as defined above with two equivalents of the methyl ester or the 2,2,2-trichloroethyl ester of glycine or N-alkyl($C_1$-$C_4$) glycine in a suitable aprotic solvent such as tetrahydrofuran, dimethylformamide or dioxane. The sulfonyl chlorides are obtained by reacting an alcohol of the formula HO($CH_2$)$_r$$R_b$ wherein r and $R_b$ are as defined hereinabove with a sulfite salt such as sodium sulfite in an aqueous lower alkanol at reflux to give compounds of the formula HO($CH_2$)$_r$$SO_3$Na which are reacted with p-nitrophenylchloroformate in a dry polar aprotic solvent such as dimethylformamide or dimethylsulfoxide in the presence of a suitable amount of a tertiary amine such as trialkylamine or pyridine at 0° to 20° C. to give compounds of the formula $R_c$OCOO($CH_2$)$_r$-$R_d$ wherein $R_c$ is p-nitrophenyl, r is 4–9, and $R_d$ is a trialkyl($C_1$-$C_4$) ammonium or pyridinium which are treated with thionyl chloride either using excess thionyl chloride as solvent or using an aprotic solvent such as dimethylformamide.

When Z is —O—, Q is $R_{16}CH_2COOH$ and $R_{15}$ is —N($R_{15}$)$SO_2$— the compounds are prepared by treating a steroid of the formula StOH wherein St has the meaning defined in Formula VII with a compound of the formula $R_c$OCOO($CH_2$)$_r$N($R_{16}$)$SO_2CH_2COOCH_3$ (Formula XXXV) wherein r and $R_{16}$ are as defined in Formula I and $R_c$ is p-nitrophenyl in a dry polar solvent such as dimethyl formamide or dimethylsulfoxide in the presence of an acylation catalyst such as DMAP or N-methylimidazole. The reaction will proceed at room temperature but is preferably carried out at about 40° to 50° C. The resulting ester is then selectively hydrolyzed with an aqueous acid such as hydrochloric, sulfuric or methanesulfonic. The Formula XXXV compounds are prepared by reacting p-nitrochloroformate with an alcohol ester of the formula HO($CH_2$)$_r$N($R_{16}$)$SO_2CH_2COOCH_3$ in a dry polar aprotic solvent in the presence of a tertiary amine. The alcohol esters are obtained by reacting a sulfonyl chloride of the formula $ClSO_2CH_2COOR_g$ wherein $R_g$ has the meaning defined hereinabove with an amino alcohol of the formula HO($CH_2$)$_r$NH($R_{15}$) in an aprotic solvent and a stoichiometric amount of a tertiary amine. The amino alcohols are commercialy available or prepared by reacting a primary amine with a halo alcohol, HO($CH_2$)halo, and the sulfonyl chloride is prepared by well known procedures.

When Z is a bond and Q is CO-COOH the compounds are prepared by treating a steroid of the Formula XXVI wherein $X_5$ is iodo with a slight molar excess of a compound of the formula HOCO($CH_2$)$_r$COCOOH (Formula XXXVI) in a polar aprotic solvent such as dimethylformamide or dimethylsulfoxide at room temperature in the presence of two molar equivalents of an organic base such as a tertiary amine but more preferably a bicyclic amidine such as DBU. The Formula XXXVI compounds are obtained by treating appropriate diesters of dicarboxylic acids with one equivalent of diethyloxalate in the presence of one equivalent of sodium ethoxide in ethanol, or preferably in an aprotic solvent such as diethylether to give after aqueous workup intermediate triesters of the formula

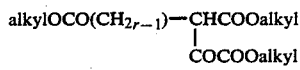

wherein alkyl has 1 to 4 carbon atoms, which are then treated with 4N HCl at 60°–70° C. for 5 to 10 hours to give the α-ketodicarboxylic acids.

The compounds of Formula I wherein Z is —O— and Q is —CO—COOH are prepared by treating a steroid of the formula StOH wherein St is as defined in Formula VII with a small molar excess of a compound of the formula $R_c$OCOO($CH_2$)$_r$COCOOR$_g$ (Formula XXXVII) wherein r is as defined in Formula I, R is p-nitrophenyl, and $R_g$ has the meaning defined hereinabove in a polar aprotic solvent at 40° to 50° C. in the presence of one equivalent of organic base such as DMAP or a mixture of DMAP and pyridine and selectively hydrolyzing the resulting ester with aqueous acid. The compounds of Formula XXXVII are prepared by treating compounds of the formula HO($CH_2$)$_r$COCOOH (Formula XXXVIII) with two equivalents each of triethylamine and p-nitrophenylchlorocarbonate in a suitable solvent such as tetrahydrofuran at 0° C. for 20 minutes then adding excess methanol or 2,2,2-trichloroethanol and one additional equivalent of triethylamine and allowing the mixture to warm to room temperature. The compounds of Formula XXXVIII are obtained by treating a lactone of the formula

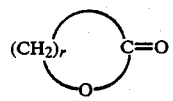

Formula XXXIX with aqueous potassium hydroxy and treating the resulting potassium alkanoate salt with iodoacetamide to give compounds of the formula HO($CH_2$)$_r$COOCH$_2$CONH$_2$ which are treated with a stoichiometric amount of chlorotriphenylmethane in dry, pyridine at 100° C. for one hour to give compounds of the formula $R_e$O($CH_2$)$_r$COOCH$_2$CONH$_2$ wherein r is 2 to 8 and $R_e$ is triphenylmethyl. The triphenylmethyl derivatives are treated with aqueous base to give $R_e$O($CH_2$)$_r$COOH which compounds are treated with excess thionyl chloride then heated at 150° to 200° C. for about two hours in the presence of excess cuprous cyanide to give $R_e$O($CH_2$)$_r$COCN which compounds are treated with concentrated HCl for several days to give HO($CH_2$)$_r$COCOOH compounds.

The compounds of Formula I wherein Z is a bond and Q is —CON($R_7$)CH($R_{18}$)COOH are prepared by activating the carboxylic acid of a compound of the formula St—O—CO-($CH_2$)$_r$COOH (Formula XLI) by treatment with stoichiometric amounts of isobutylchloroformate and triethylamine in a dry aprotic solvent at −10° to 0° C. for 15 to 20 minutes, then adding an appropriate amino acid along with one equivalent of pyridine or triethylamine. Appropriate amino acids for this reaction and the 5 one described below are glycine, sarcosine, alanine, aspartic acid, proline, glutamic acid, serine, threonine, cysteine, methionine, tyrosine, or glycylglycine. The compounds of Formula XLI are prepared by treating a compound of Formula XXVI, i.e., St$X_5$, with a stoichiometric amount of a sterically hindered tertiary amine such as diisopropylethylamine and a large excess of a dicarboxylic acid of the formula HOOC($CH_2$)$_r$COOH in a polar aprotic solvent. When $X_5$ in Formula XXVI is iodo the reaction is carried out at room temperature and when $X_5$ is O-mesyl the reaction is carried out at about 45° to 60° C.

When Z is —O— and Q is —CON($R_{17}$)CH($R_{18}$)COOH the compounds are prepared by treating a steroid StOH wherein St has the meaning defined in Formula VII with a compound of the formula $R_c$O-COO(CH$_2$)$_r$CON($R_{17}$)CH($R_{18}$)COOCH$_3$(Formula XL) wherein r, $R_{17}$ and $R_{18}$ are as defined in Formula I and $R_c$ is p-nitrophenyl, in a polar aprotic solvent such as dimethylformamide or dimethylsulfoxide at 40° to 50° C. in the presence of one equivalent of a tertiary amine such as pyridine and a catalytic amount of dimethylaminopyridine or N-methylimidazole and subsequently hydrolyzing the thus formed methyl ester derivative to the corresponding free acid using aqueous acid. The Formula XL compounds are prepared by treating a lactone of Formula XXXIX with a methyl ester or a 2,2,2-trichloroethyl ester of an appropriate amino acid as identified above in a polar aprotic solvent in the presence of one equivalent of a non-nucleophilic base at elevated temperature to give compounds of the formula HO(CH$_2$)$_r$CON($R_{17}$)CH($R_{18}$)COOCH$_3$ which are treated with a slight excess of p-nitrophenylchlorocarbonate in a dry aprotic solvent at 0° to 20° C. in the presence of a stoichiometric amount of pyridine or a tertiary amine.

The methyl ester of the compounds described herein can be hydrolyzed to the free acid by heating in aqueous acid by well known procedures. The 2,2,2-trichloroethyl ester of the compounds described hereinabove can be converted to the free acid by treatment with zinc and acetic acid as generally described in J. Am. Chem. Soc. 88, 852 (1966). The salts of the compounds of Formula I, are prepared by treating the acid with a suitable base as generally described hereinabove.

As indicated hereinbefore the various parent steroid starting materials, i.e., StOH and StX$_5$ are known in the art or are prepared by procedures well known in the art.

PREPARATION OF COMPOUNDS OF FORMULA I WHEREIN $R_{11}$ IS —CH$_2$CH$_2$COOH

The compounds are generally prepared by treating one equivalent of 21-hydroxy steroid otherwise corresponding to Formula I with 1.2 equivalents of succinic anhydride and 0.05 equivalents of potassium carbonate in a tertiary amine, e.g., pyridine. The reaction is carried out at room temperature with stirring for about 20 hours then the reaction mixture was partitioned between methylene chloride and water. The organic phase is washed with water, dried over sodium sulfate, concentrated and the resulting residue crystallized from an appropriate solvent. To form a salt, e.g., the sodium salt, the crystallized compound is stirred in methanol (ratio of 20 ml of methanol to 1 g of steroid) and treated with 0.95 equivalents of sodium bicarbonate which was dissolved in a minimum volume of water. The liquids are concentrated, the residue lyophilized overnight after which the solid is triturated with an appropriate solvent and dried.

Following the method of the above General Preparation the following compounds were prepared:

21-(3-Carboxy-1-oxopropoxy)pregna-1,4,9(11),16-tetraene-3,20-dione, m.p./solvent: decomp 200° C., acetonitrile.

21-(3-Carboxy-1-oxopropoxy)-17α-hydroxypregna-4,9(11)diene-3,20-dione, sodium salt, m.p./solvent: 251°-252° C., acetone.

21-(3-Carboxy-1-oxopropoxy)-17α-hydroxy-16α-methylpregna-4,9(11)-diene-3,20-dione, sodium salt, m.p. 183° C. decomp.

21-(3-Carboxy-1-oxopropoxy)-16α,17α-dihydroxypregna-4,9(11)diene3,20-dione, sodium salt, m.p./solvent: 120°-130° C. decomp, acetone/ether.

21-(3-Carboxy-1-oxopropoxy)-16α,17α-dihydroxypregna-1,4,9(11)triene-3,20-dione, sodium salt, .1.45 H$_2$O, m.p./solvent: 153°-155° C. decomp, acetone/ether.

21-(3-Carboxy-1-oxopropoxy)-17α-hydroxy-16β-methylpregna-1,4,9-(11)triene-3,20-dione, sodium salt.H$_2$O, m.p.: 230°-235° C., decomp.

It may be desirable to protect various functions found on the 21-hydroxy steroid starting material, e.g., ketone groups or hydroxy groups at positions other than C-21. Protection and subsequent deprotection of functional groups on the parent steroid is accomplished by procedures well known in the art and/or as illustrated in the specific examples which follow.

EXAMPLE 1

N-methyltaurine amide of 17α-hydroxy-4,9(11)pregnadiene-3,20-dione-21-hemisuberate [Formula I: $R_1$=CH$_3$; $R_2$ and $R_3$ form a double bond; C-1 is saturated; $R_4$, $R_5$, $R_6$ and $R_9$=H; $R_{10}$=α-OH; $R_{11}$=—Y—(CH$_2$)$_n$—X—(CH$_2$)$_m$—SO$_3$H; Y=bond; n=6; X=—CON(CH$_3$); m=2.]

A 20.0 g sample (0.058 mol) of 17α,21-dihydroxy-4,9(11)pregnadiene-3,20-dione was dissolved in 100 ml of pyridine and treated with 9.94 g (0.087 mol) of methanesulfonyl chloride. After five hours the mixture was partitioned between methylene chloride and water. The organic phase was dried with sodium sulfate and concentrated. An insoluble material was filtered after the partition. The NMR spectra of the filtered solid and the methylene extract were the same and were consistent with the 21-mesylate. The combined mesylate fractions were refluxed in 600 ml of acetonitrile with 20 g of sodium iodide for 1.5 hours. The reaction was filtered through celite and concentrated to dryness. The residue was crystallized from hexane and acetone to yield a 17.8 g first crop of iodide 1B. A 4.74 g (0.0105 mol) sample of the iodide was dissolved in 15 ml of DMF and was treated with the disodium salt of U-69794A, which is the N-methyltaurine amide of suberic acid (sodium salt), which was prepared as follows: 5.00 g (0.0314 mol) of the N-methyltaurine amide of suberic acid (sodium salt) in 50 ml of methanol was reacted with 3.6 ml of 4.4 M sodium methoxide in methanol. This disodium salt was concentrated to dryness and added to the DMF solution of the iodide. The reaction of the iodide and the disodium salt was stirred for 20 hours at 40°. The mixture was then treated with ethyl acetate. The crystals which resulted were filtered and then partitioned between methylene chloride/i-propanol and a pH4 sodium sulfate aqueous solution. The organic phase was dried over sodium sulfate and concentrated. The residue was chromatographed on silica gel with a methanol/methylene chloride gradient (2% to 15%) to yield 370 mg of final product.

EXAMPLE 2

(a) 6α-Methylcortisone 21-acetate

Jones reagent (15 ml) was added rapidly to a stirred cold solution of 20.92 g of 11β,17α,21-trihydroxy-6α-methyl-4-pregnene-3,20-dione, 21-acetate in 600 ml of acetone (5° to 15° C.). The mixture was allowed to stir for 35 minutes after which isopropanol (15 ml) was added, then (after cooling to 15° C.) water was added slowly to a volume of 3 liters. The product was collected, washed thoroughly with cold water and dried at 50° C. under vacuum to give 19.4 g (93%) of 6α-methylcortisone 21-acetate., one major spot by TLC (Rf 0.5, 5% CH$_3$OHCH$_2$Cl$_2$).

(b) 6α-Methylcortisone

A solution of 19.3 g of 6α-methylcortisone 21-acetate in methanol (1200 ml) was heated to reflux, then cooled under nitrogen to 25° C. Nitrogen-purged 10% aqueous potassium carbonate (48.2 ml) was added, the mixture was stirred for about 0.5 hour and then was acidified with acetic acid (4.8 ml). Water (1200 ml) was added, the mixture was concentrated under vacuum and extracted with ethyl acetate. The extract was washed with brine, dried over sodium sulfate and evaporated. The residue was crystallized from acetone-hexane to give 11.5 g (66%) of 6α-methylcortisone; one spot by TLC (Rf 0.5, 10% CH$_3$OH-CH$_2$Cl$_2$).

(c) 6-Methyl-17α-21-dihydroxypregn-5-ene-3,11,20-trione-3,20-bis-ethylene ketal Benzene (80 ml) was distilled from a stirred mixture of 17.0 g of 6α-methylcortisone, ethylene glycol (31 ml) and benzene (625 ml). p-Toluene sulfonic acid hydrate (0.31 g) was then added, the mixture ws heated under reflux (water separator) for 4.5 hours and then was cooled in ice. Aqueous 1N KHCO$_3$ (400 ml) was added, the organic phase ws washed with water and brine, then filtered through sodium sulfate and evaporated. Chromatography of the residue on 2 kg of silica gel packed in 10% acetone-CH$_2$Cl$_2$ and elution (250 ml fractions) with 10% to 70% acetone-CH$_2$Cl$_2$ gave 14.7 g (70%) of the title compound (c) as a white foam. $^1$H NMR: 1.68 (6—CH$_3$), 1.20 (19—CH$_3$), 0.80 (18—CH$_3$); $^{13}$C NMR: 220 (C-11), 133.10 (C-5), 124.35 (C-6), 112.00 (C-20), 108.76 (C-3), 85.68 (C-17), 66.55 (C-21), 64.29, 63.59, 63.38 (—OCH$_2$CH$_2$O—), 59.54 (C-9), 19.13, 17.82, 15.56 (CH$_3$—).

(d) 6-Methyl-11α,17α,21-trihydroxypregn-5-ene-3,20-dione-3,20-bis-ethylene ketal A solution of 14.45 g of the compound from Example 2(c) in a mixture of dioxane (540 ml), ether (155 ml) and absolute alcohol (92 ml) was added slowly to 2.26 liters of liquid ammonia. The cooling bath was removed and lithium wine (15.4 g) was added in small pieces. The mixture was stirred for 2 hours, the blue color was discharged with alcohol, and then ammonia was evaporated (bath 50° to 60° C.). The residue was partitioned (ethyl acetate-water); the extract was washed with brine, dried over sodium sulfate and evaporated to give 13.4 g (92%) of the title compound of Example 2(d); one major spot by TLC (10% CH$_3$OH—CH$_2$Cl$_2$).

(e) 6α-Methyl-11α,17α,21-trihydroxypregn-4-ene-3,20-dione

A solution of 13 g of the compound from Example 2(d) in 60% formic acid (113 ml) was heated quickly to 75° C. (steam bath) and held at 75° to 90° C. for 5 minutes. The mixture was then cooled (methanolice), diluted with ethyl acetate (400 ml) and 200 ml of ice and water, and then nearly neutralized (pH 5-6) with 45% aqueous KOH (127 ml). The aqueous layer was extracted with ethyl acetate (2×250 ml) and the extracts were washed with 1N KHCO$_3$ and brine, then were dried over MgSO$_4$. The residue was chromatographed on 1.4 kg of silica gel. A mixture of products (6.4 g) was eluted with 5% CH$_3$OH-CH$_2$Cl$_2$. Continued elution with 10% CH$_3$OH—CH$_2$Cl$_2$ gave 5.56 g of crude (5). The 6.4 g fraction was retreated with formic acid and the residue was hydrolyzed with K$_2$CO$_3$ in aqueous methanol. Chromatography gave an additional 2.5 g of crude title compound Example 2(e).

(f) 11α,21-Diacetyloxy-17α-hydroxy-6α-methyl-pregn-4-ene-3,20-dione

A solution of 5.2 g of crude product from Example 2(e) in pyridine (20 ml) and acetic anhydride (40 ml) was allowed to stand 16 hours at 25° C. The reaction mixture was quenched with ice water to give a gummy precipitate. An ethyl acetate extract of the product was washed with 1N HCl, H$_2$O, aqkueous NaHCO$_3$ and brine, then was dried over Na$_2$SO$_4$. The dried extract was evaporated and the residue chromatographed on 500 g of silica gel. Elution with 3% CH$_3$OH-CH$_2$Cl$_2$ gave the title compound. A sample was further purified by crystallization from aqueous CH$_3$OH; m.p., 238°-241° C.; $^1$H NMR: 5.85 (4—H), 5.25 (11β—H), 5.0 (dd, 21-CH$_2$), 3.7 (—OH), 2.18, 2.06 (CH$_3$CO—), 1.28 (19—CH$_3$), 1.11 (d, 6—CH$_3$), 0.77 (18—CH$_3$). Analysis calculated for C$_{26}$H$_{36}$O$_7$: C, 67.8; H, 7.88. Found: C, 67.5; H, 8.04.

(g) 11α-Acetyloxy-17α,21-dihydroxy-6α-methyl-pregn-4-ene-3,20-dione

A solution of 4.0 g of crude product from Example 2(f) in methanol (225 ml) was heated to boiling, then cooled to 25° C. under N$_2$ and 9.2 ml of 10% K$_2$CO$_2$ (N$_2$-purged) was added. The mixture was allowed to stand for about 20 minutes, then acetic acid (0.9 ml) and water (220 ml) was added. Concentration at reduced pressure gave a white crystalline precipitate which was collected, washed with water and dried to give 2.6 g of the title compound of Example 2(g). A sample was crystallized from CH$_2$Cl$_2$—CH$_3$OH; m.p., 274°-278° C.; $^1$H NMR: 5.65 (4—H), 5.15 (11β—H), 1.98 (CH$_3$C=O), 1.21 (19—CH$_3$), 1.02 (d, 6—CH$_3$), 0.61 (18—CH$_3$).

(h) 11α-Acetyloxy-21-(3-carboxy-1-oxopropoxy)-17-hydroxy-6α-methylpregn-4-ene-3,20-dione A solution of 5.73 g of the product from Example 2(g) and 5.47 of succinic anhydride in pyridine (46 ml) was allowed to stand 20 hours at 25° C. The reaction mixture was then added slowly to a stirred mixture of ice (450 ml), H$_2$O (450 ml) and concentrated HCl (45 ml). The mixture was allowed to warm to 25° C., the precipitate was collected, washed thoroughly with water and dried in vacuum to give 6.18 g (87%) of the title compound Example 2(h). A 0.58 g sample was crystallized from acetone-hexane to give 0.50 g of crystals; m.p., 104°-110° C. Analysis calculated for C$_{28}$H$_{38}$O$_9$ (518.58): C, 64.85; H, 7.38. Found: C, 64.17; H, 7.69; UV: λmax 239 (ε14350).

(i)
11α-Acetyloxy-21-(3-carboxy-1-oxopropoxy)-17-hydroxy-6α-methylpregn-4-ene-3,20-dione, sodium salt, monohydrate To a solution of 6.162 g (11.88 mmol) of the product from Example 2(h) in acetone (80 ml) and water (25 ml) was added a solution of 1 g (11.9 mmol) of $NaHCO_3$ in 40 ml of water (20 ml rinse). The solution was filtered through hardened filter paper and the filtrate freeze dried to give the title compound Example 2(i) as a white powder. Analysis calculated for $C_{28}H_{37}NaO_9 \cdot H_2O$ (558.61): C, 60.2; H, 7.04; $H_2O$, 3.22. Found: C, 59.16; H, 6.87; $H_2O$, 3.35; UV: λmax 246 nm (ε15200).

EXAMPLE 3

(a)
17α,21-Dihydroxy-6α-methyl-pregn-1,4,9(11)-triene-3,20-dione

A 13.58 g sample of 21-acetoxy-17α-hydroxy-6α-methylpregna-1,4,9-(11)-triene-3,20-dione in methanol (850 ml) was hydrolyzed with 10% potassium carbonate (34 ml). The reaction mixture was acidified, diluted with water and concentrated to give a gummy precipitate which was dissolved in ethyl acetate. The extract was washed with water and brine, then dried over sodium sulfate and evaporated. Crystallization of the residue from acetone-hexane gave the title compound Example 2(a), m.p. 204°–206° C.; one spot by TLC (10% $CH_3OH$—$CHCl_3$).

(b)
21-(3Carboxyl-1oxopropoxy)-17α-hydroxy-6α-metholpregna-1,4,9(11)-triene-3,20dione A solution of 7.39 g of the compound from Example 3(a) and 8.3 g of succinic anhydride in pyridine (69.1 ml) was allowed to stand overnight at 25° C. The reaction mixture was then added slowly to a stirred mixture of ice (690 ml), water (690 ml) and concentrated HCl (69 ml). The mixture was allowed to warm to 25° C., then the product was collected, washed thoroughly with water and dried under vacuum to give 8.35 g of the title compound Example 3(b), m.p., 243°–246° C.; one spot by TLC (10% acetone-$CH_2Cl_2$). Analysis calculated for $C_{26}H_{32}O_7$ (456.52): C, 68.4; H, 7.07. Found: C, 68.08; H, 7.14; $H_2O$ (0.36%); UV: λmax 239 nm (ε15550).

(c)
21-(3-Carboxy-1-oxopropoxy)-17α-hydroxy-6α-methylpregna-1,4,9(11)-triene-3,20-dione, sodium salt, hemihydrate A 4.565 g sample of the compound from Example 3(b) was converted to the sodium salt essentially as described in Example 2(i) except the amount of $NaHCO_3$ was reduced to 0.84 g. A 4.71 g sample of the title compound Example 3(c) was obtained. Analysis calculated for $C_{26}H_{31}NaO_7 \cdot 0.5 \ H_2O$ (487.52): C, 64.05; H, 6.63; $H_2O$, 1.85. Found: C, 60.94; H, 6.37; $H_2O$, 2.09; UV: λmax 242 nm (ε15350).

EXAMPLE 4

11α-Acetoxy-21-(3-carboxy-1-oxopropoxy)-17α-hydroxy-4-pregna-3,20-dione

Cortisone was protected with a bismethylenedioxy group on the C-21 side chain and with a ketal group at C-3. A mixture of 11.1 g of the protected ketone was dissolved in 110 ml of dioxane, 76 ml of ethanol and 35 ml of ethyl ether. Liquid ammonia (700 ml) was added. Lithium (12.7 g) was added incrementally. The reaction was stirred for 3.5 hours and 46 g of ammonium chloride was added. The ammonia was removed. The reaction was extracted with ethyl acetate and water. The organic phase was extracted with brine, dried over sodium sulfate and concentrated. The reaction yielded 9.00 g of a foam. An 8.30 g sample of this foam was dissolved in 20 ml of pyridine and treated with 4.15 g of acetic anhydride. After 20 hours, the reaction was partitioned with ether and water. The organic phase was washed with sodium bicarbonate. Methylene chloride was added and the organic phase was washed with brine, dried over sodium sulfate and concentrated. The residue was triturated with 1:1 ether/hexane to yield 6.25 g of 11-acetoxy derivative. This sample was dissolved in 100 ml of acetone and treated with 5 ml of 6N HCl. The reaction was stirred for 2.6 hours and was then partitioned between methylene chloride and water. The organic phase was then washed with aqueous sodium bicarbonate, dried over sodium sulfate and concentrated to yield 6.82 g of the 3-keto-11-acetate. This material was stirred in 100 ml of formic acid for 4.5 hours. The reaction was concentrated and the residue was stirred with 20 ml methanol and 5 ml of 20% potassium carbonate in water for 5 minutes. The mixture was partitioned between methylene chloride and water. The organic phase was partitioned with aqueous sodium bicarbonate and then dried over sodium sulfate. The organic phase was concentrated and the residue was crystallized from ethyl acetate/hexane to yield 2.59 g first crop of the product. This 2.59 g sample was dissolved in 10 ml of DMF and was treated with 0.74 g of succinic anhydride and 25 mg of potassium carbinate. The mixture was stirred at 50° C. for two hours. The mixture was partitioned between methylene chloride and water. The organic phase was washed with water twice and was then dried over sodium sulfate. The methylene chloride solution was concentrated to yield 3.03 g of the title product.

EXAMPLE 5

21-(3-Carboxy-1-oxopropoxy)-17α-hydroxy-11α-hydroxy-pregna-4-ene-3,20-dione, sodium salt (a) Bis-Methylene-dioxy ketal protected 11-epi-cortisol A 21.72 g (0.052 mol) sample of the bis-methylenedioxy (BMD) protected δ-4,3,11-di-one was stirred in 500 ml of methylene chloride with 11.64 g (0.079 mol, 1.5 equiv) of triethylorthoformate, 3.90 g (0.063 mol, 1.2 equiv) of ethylene glycol which had been distilled from sodium and 0.5 g of toluene sulfonic acid. After two days another 5.8 g of triethylorthoformate and 2 g of ethylene glycol were added. The reaction proceeded to completion very quickly. The reaction mixture was partitioned with aqueous sodium bicarbonate and dried over sodium sulfate. The organic phase was concentrated and crystallized from ether to give 11.13 g of a first crop which was clean by thin layer chromatography (TLC) and nmr. This material was dissolved in 110 ml of dioxane, 76 ml of ethanol, 35 ml of ether and added to a 3L round bottom flask. About 1000 ml of ammonia was condensed into the flask. To the vigorously stirred reaction was added 12.7 g of lithium wire. The reaction was stirred for 3.5 h at which time the color was discharged. Then, nitrogen gas was bubbled through the reaction until the mixture was concentrated. Then, ammonium chloride and, after stirring, water were added. The reaction was partitioned between ethyl acetate and water. The organic phase was washed with brine, dried over sodium sulfate and concentrated to yield 9.00 g of a foam which was clean by TLC. This material was used in subsequent reactions without further purification. In a similar reaction, 124 g of the BMD protected steroid, 66.5 g of triethylorthoformate, 23 g of ethylene glycol, 1L of methylene chloride and 0.6 g of toluene sulfonic acid yielded 76.76 g of crystalline product.

(b) 11 αAcetate, Δ4,3-one

A solution of 8.30 g of the protected 11-epi-cortisol from 5(a) in 20 ml of pyridine was stirred with 4.15 g of acetic anhydride for 20 hours. The mixture was partitioned between ether and water. The organic phase was washed once with water, once with aqueous sodium bicarbonate and then diluted with methylene chloride. The organic phase was washed with brine, dried over sodium sulfate and concentrated. The residue was triturated with 1:1 ether/hexane to yield 6.25 g of a white solid, the 11αO-acetate. This material was dissolved in 100 ml of acetone and treated with 5 ml of 6N HCl for 2 hours. The reaction was concentrated. The residue was partitioned between methylene chloride and water. The organic phase was then partitioned with aqueous sodium bicarbonate, dried over sodium sulfate and concentrated. The organic phase was concentrated to yield 6.82 g of the 3-keto 17,21-BMD 11α-O-acetyl steroid. This was stirred at 50° C. in 100 ml of 90% formic acid for 4.5 hours. The reaction was concentrated and the residue was partitioned with methylene chloride and water. The organic phase was dried over sodium sulfate and concentrated. Methanol (50 ml) and 10 ml of 22% potassium carbonate were added and stirred for 10 minutes to hydrolyze the formate esters. The mixture was partitioned between methylene chloride and water. The organic phase was dried over sodium sulfate and concentrated. The residue was crystallized from ethyl acetate and hexane. The crystals were washed with ether to yield a 3.57 g first crop. The residue was chromatographed to yield an additional 600 mg of product.- m/e=404. Anal. Calcd for $C_{23}H_{32}O_6$. Calcd/Found: C, 68.29//67.43; H, 7.97/7.89.2.

A 2.49 g (0.00616 mol) sample of the α-acetocy compound from above was dissolved in 10 ml of dimethylformamide and was treated with 0.74 g (0.0074 mol) of succinic anhydride and 25 mg of potassium carbonate. The mixture was stirred for 2 hours at 50° C. The mixture was partitioned between methylene chloride and water. The organic phase was washed twice with water, dried over sodium sulfate and concentrated to yield 3.03 g of a yellow foam. This was crystallized from ether and ethyl acetate to yield a 1.45 g first crop and a 160 mg second crop, m/e=504. Anal. Calcd for $C_{27}H_{36}O_9$. Calcd/Found: C, 64.27/64.56; H, 7.19/7.55.

A 1.55 g (3.07 mmol) sample of the hemisuccinate was dissolved in 1:1 acetone/methanol and treated with 0.26 g (3.0 mmol) of sodium bicarbonate in 20 ml of water. The solution was swirled for 2 minutes, concentrated and lyophilized overnight. The residue was triturated with acetonitrile and ether to yield 1.40 g of a white solid which softened at 240° C. and then decomposed. m/e=526. Anal. Calcd for $C_{27}H_{35}O_9Na.\frac{1}{2}H_2O$. Calcd/Found: C, 59.16/58.10; H, 6.88/6.70; water 3.94/3.55.

EXAMPLE 6

21-(3-Carboxy-1-oxopropoxy)-17α-hydroxy-11α-[(4-bromo)-phenyloxomethoxy]pregna-4-ene-3,20-dione, sodium salt (a) 11-epi-Cortisol, 17,21-acetonide The 11-epi-cortisol was chromatographed (silica gel, 2% to 8% methanol in methylene chloride), and a 13 g sample was dissolved in 500 ml of methylene chloride and treated with 10 ml of 2-methoxypropene and 50 mg of toluene sulfonic acid. After 2 hours, the mixture was treated with 50 ml of acetone to destroy any 3-0-methyl ethers. The mixture was concentrated and chromatographed (silica gel, 1:1 ethyl acetate/hexane) to yield 10.0 g of pale yellow crystals which were recrystallized from ether and hexane to give an 8.03 g first crop.

(b) 11α-O-4-Bromo-benzoate of d 11-epi-cortisol

A solution of 1.88 g (0.0047 mol) of the acetonide of 11-epi-cortisol from 6(a) was dissolved in methylene chloride (25 ml) and was treated with 1 ml of pyridine and 1.23 g (0.0056 mol, 1.2 equiv) of 4-bromobenzoyl chloride. The mixture was stirred for 17 hours and was then partitioned between ether and aqueous sodium bicarbonate. The organic phase was washed with brine and dried over sodium sulfate to give a fairly clean material. The organic phase was concentrated and the residue was chromatographed on silica gel (10% ethyl acetate/hexane) to yield 1.45 g of pure product and 120 mg of a contaminated fraction. Anal. Calcd for $C_{31}H_{37}BrO_6$. Calcd/Found: C, 63.58/63.33; H, 6.37/6.45.

The acetonide was deprotected by heating at 45° C. a solution of 700 mg of the acetonide and 0.2 ml of TFA in ethanol for 8 hours. The reaction was partitioned between methylene chloride and aqueous sodium bicarbonate. The organic phase was dried over sodium sulfate and concentrated to yield 600 mg (0.0011 mol) of the 21—OH compound. This material was dissolved in 25 ml of methylene chloride and treated with 0.14 g (0.00143 mol) of succinic anhydride, 0.14 g triethylamine and 50 mg of DMAP. The solution was stirred for 4 hours and was then concentrated. The residue was crystallized from ether to yield 430 mg (0.67 mmol) of the pale yellow triethylamine salt. This material was dissolved in methanol and was treated with 0.054 g (0.64 mmol) of sodium bicarbonate in water. The mixture was concentrated and lyophilized overnight. The residue was triturated with acetone and ether to yield 250 mg of the solid product which softened at 174 and decomposed at 240° C.

EXAMPLE 7

21-(3-Carboxy-1-oxopropoxy)-17α-hydroxy-11α-(1-oxo-propoxy)pregna-4-ene-3,20-dione, sodium salt A solution of 4.80 g (0.0123 mol) of the acetonide of 11-epi-cortisol in 20 ml of dry pyridine was treated with 1.20 g (0.013 mol) of propionyl chloride at 0° C. The reaction was warmed to room temperature and stirred for 19 hours. The mixture was partitioned between ether and (1) water, (2) 2% HCl, (3) water, (4) aqueous sodium bicarbonate, and (5) brine. The mixture was concentrated. The residue was crystallized from ether and hexane to yield a 3.74 g first crop. This material was deprotected in 200 ml of acetone and 8 ml of 5% HCl at 60° C. for one hour. The reaction was concentrated and chromatographed on silica gel (2 to 4% methanol in methylene chloride) to yield 2.60 g (50% from the starting acetonide) of the desired 11-O-propionate, 21-alcohol. A 2.50 sample of this alcohol was reacted for 20 hours in 15 ml of dry dimethyl formamide with 0.598 g of succinic anhydride and a trace of potassium carbonate. The reaction was concentrated to give a residue which was triturated with ether and hexane to give 2.38 g (78%) of a white solid hemisuccinate. This material was dissolved in 20 ml of methanol and 1 ml of water. The solution was stirred for 10 min with 0.401 g of sodium bicarbonate. The reaction was lyophilized. The residue was triturated with ether to yield 2.37 g of a white solid, turned to a glass at 117°–120° C.

EXAMPLE 8

21-(3-Carboxy-1-oxopropoxy)-17α-hydroxy-11α-[(4-chloro)phenyloxymethoxy]pregna-4-ene-3,20-dione, sodium salt A solution of 4.00 g (0.0102 mol) of the acetonide of 11-epi-cortisol in 20 ml of dry pyridine was treated with 1.20 g (0.0104 mol) of p-chlorobenzoyl chloride at 0° C. The reaction was warmed to room temperature and stirred for 19 hours. The mixture was partitioned between ether and (1) water, (2) 2% HCl, (3) water, (4) aqueous sodium bicarbonate, and (5) brine. The mixture was concentrated. The residue was crystallized from ether and hexane to yield a 3.54 g first crop. This material was deprotected in 200 ml of acetone and 8 ml of 5% HCl at 60° C. for one hour. The reaction was concentrated and chromatographed on silica gel (2 to 4% methanol in methylene chloride) to yield 3.56 g (69% from the starting acetonide) of the desired 11-O-(4-chloro)benzoate, 21-alcohol. A 3.56 g sample of this alcohol was reacted for 20 hours in 10 ml of dry dimethyl formamide with 0.700 g of succinic anhydride and a trace of potassium carbonate. The reaction was concentrated to give a residue which was triturated with ether and hexane to give a white solid hemisuccinate, decomp 155°–175° C. This material was dissolved in 20 ml of methanol and 1 ml of water. The solution was stirred for 10 minutes with 0.14 g of sodium bicarbonate. The reaction was lyophilized. The residue was triturated with ether to yield a white solid hemisuccinate.

EXAMPLE 9

21-(3-Carboxy-1-oxopropoxy)-17α-hydroxy-11α-(2-methyl-1-oxopropoxy)pregna-4-ene-3,20-dione The 17,21-acetonide of 11-epi-cortisol (5.00 g, 0.0128 mol) was dissolved in 20 ml of pyridine and reacted with 1.36 g (0.013 mol) of dimethylacetyl chloride for 21 hours at room temperature under nitrogen. The mixture was partitioned between ether and aqueous sodium bicarbonate. The organic phase was washed with brine, dried over sodium sulfate and concentrated. The residue was dissolved in 150 ml of acetone. To this solution was added 10 ml of 5% aqueous HCl. The mixture was stirred at 60° C. for one hour. The reaction was partitioned between methylene chloride and aqueous sodium bicarbonate. The organic phase was dried over sodium sulfate and concentrated. The residue was chromatographed on silica gel (4% methanol/methylene chloride) to yield 4.43 g which was crystallized from ether to yield 3.58 g of the 21-alcohol. Anal. Calcd for $C_{25}H_{36}O_6$. Calcd/Found: C, 69.42/69.68; H, 8.39/8.51.

This material was dissolved in 15 ml of DMF and was reacted with 0.83 g of succinic anhydride and a trace of potassium bicarbonate at 65° C. for 3 hours. The reaction was concentrated. The residue was partitioned between methylene chloride and 1% HCl. The organic phase was washed with water, dried over sodium sulfate, and concentrated to yield 3.79 g of product. This was treated with 0.62 g of sodium bicarbonate in water/methanol. The solution was lyophilized and the residue was crystallized from acetonitrile and ether to yield 2.429 g of product, decomp 223–225, mass spec supports structure. Anal. Calcd for $C_{29}H_{39}O_9Na \cdot H_2O$. Calcd/Found: C, 60.83/59.79; H, 7.22/6.94; $H_2O$, 3.15/1.70.

EXAMPLE 10

21-(3-Carboxy-1-oxopropoxy)-17α-hydroxy-11α-(2,2-dimethyl-1-oxopropoxy)pregna-4-ene-3,20-dione The 17,21-acetonide of 11-epi-cortisol (4.50 g, 0.0115 mol) was dissolved in 30 ml of pyridine and reacted with 1.80 g (1.3 equiv, 0.015 mol) of trimethylacetyl chloride for 4 days at room temperature under nitrogen. The mixture was partitioned between ether and aqueous sodium bicarbonate. The organic phase was washed with brine, dried over sodium sulfate and concentrated. The residue was dissolved in 150 ml of acetone. To this solution was added 10 ml of 5% aqueous HCl. The mixture was stirred at 60° C. for one hour. The reaction was partitioned between methylene chloride and aqueous sodium bicarbonate. The organic phase was dried over sodium sulfate and concentrated. The residue was chromatographed on silica gel (4% methanol/methylene chloride) to yield 3.49 g of a yellow foam which was crystallized from ether to yield 1.92 g of the 21-alcohol. Anal. Calcd for $C_{26}H_{38}O_6$. Calcd/ Found: C, 69.93/69.70; H, 8.58/8.82.

This material was dissolved in 15 ml of DMF and was reacted with 0.51 g of succinic anhydride and a trace of potassium bicarbonate for 15 hours. The reaction was concentrated. The residue was partitioned between methylene chloride and 1% HCl. The organic phase was washed with water, dried over sodium sulfate, and concentrated to yield 2.55g of product. This was treated with 0.404 g of sodium bicarbonate in water/methanol. The solution was lyophilized and the residue was crystallized from acetonitrile and ether to yield 1.89 g of product, decomp 225-235, mass spec supports structure. Anal. Calcd for $C_{30}H_{41}O_9Na \cdot H_2O$. Calcd/Found: C, 61.42/57.35; H, 7.39/6.69; $H_2O$, 3.07/2.87.

EXAMPLE 11

21-(3-Carboxy-1-oxopropoxy)-17α-hydroxy-11α-(3,3-dimethyl-1-oxobutoxy)pregna-1,4-diene-3,20-dione The Δ1-, 17,21-acetonide of 11-epi-cortisol (4.90g) was dissolved in 25 ml of pyridine and reacted with 2.40 g of t-butylacetyl chloride for 6 hours at room temperature under nitrogen. The mixture was partitioned between ether and aqueous sodium bicarbonate. The organic phase washed with brine and was dried over sodium sulfate and concentrated. The residue was chromatographed on silica gel with 40/60 ethyl acetate hexane to yield 3.87 g of TLC pure product. This material was dissolved in 200 ml of acetone. To this solution was added 10 ml of 10% aqueous HCl. The mixture was stirred for 48 hours. The reaction was concentrated. The residue was partitioned between methylene chloride and aqueous sodium bicarbonate. The organic phase was dried over sodium sulfate and concentrated. The 3.55 g residue. This residue was dissolved in 20 ml of DMF and was reacted with 1.00 g of succinic anhydride and a trace of potassium bicarbonate at room temperature for 20 h. The reaction was concentrated. The residue was chromatographed on silica gel (4% methanol in methylene chloride to 4% methanol/.5% HOAc in methylene chloride) to yield 4.01 g of the hemisuccinate. This was dissolved in methanol and reacted with an aqueous solution of 0.60 g of sodium bicarbonate. The solution was lyophilized. The residue was triturated with acetone and ether to yield 2.14 g of product which was 98.6% pure by hplc, decomp 220. Anal. Calcd for $C_{31}H_{41}O_9Na \cdot H_2O$. Calcd/Found: C, 62.20/55.69; H, 7.24/ 6.18; H20, 3.01/2.24. m/e=581.

EXAMPLE 12

Δ1, 11-epi-Cortlsol, 17,21-acetonide

A solution of 29 g of the 17,21-acetonide of 11-epi-cortisol in 250 ml of dioxane was stirred at reflux with 19.72 g of DDQ for 2.5 hours. The ratio of the dienone to the enone was 65:13 by hplc. Another 5 g of DDQ was added and the mixture was refluxed for one hour. The mixture was filtered through celite and concentrated. The residue was chromatographed on silica gel (1.5% to 3% methanol in methylene chloride) to yield 10.1 g of the product. This powder was used without further purification. The yield might be improved by protection of the 11-alcohol.

EXAMPLE 13

21-(3-Carboxy-1-oxopropoxy)-17α-hydroxy-11α-[(2-furyl)

oxomethoxy]pregna-1,4-diene-3,20-dione

The Δ1-, 17,21-acetonide of 11-epi-cortisol (4.90 g) was dissolved in 25 ml of pyridine and reacted with 2.40 g of furanoyl chloride 5 for 4.5 hours at room temperature under nitrogen. The mixture was partitioned between methylene chloride and aqueous sodium bicarbonate. The organic phase was dried over sodium sulfate and concentrated. The residue was chromatographed on silica gel with ethyl acetate hexane to yield 3.52 g of TLC pure product. This material was dissolved in 100 ml of acetone. To this solution was added 10 ml of 10% aqueous HCl. The mixture was stirred for 3h. Another 5 ml of 10% HCl was added and the mixture was heated for 30 minutes at 1.25 hours. The reaction was concentrated. The residue was partitioned between methylene chloride and aqueous sodium bicarbonate. The organic phase was dried over sodium sulfate and concentrated. The 2.45 g residue had a mass spec which was consistent with the expected product. This residue was dissolved in 20 ml of DMF and was reacted with 0.60 g of succinic anhydride and a trace of potassium bicarbonate at room temperature for 24 hours. Another 0.15 g of anhydride was added and the mixture was stirred for 6 hours. The reaction was concentrated. The residue was chromatographed on silica gel (4% methanol in methylene chloride to 4% methanol/.5% HOAc in methylene chloride) to yield the hemisuccinate. This was crystallized from hot ethyl acetate to yield a 1.67 g first crop (mp 123-127) and a 0.52 g second crop (mp 118-125). By hplc, the first crop was 97% pure. Anal. Calcd for $C_{30}H_{34}O_{10} \cdot H_2O$. Calcd/Found: C, 62.99/61,70; H, 6,34/6,19. Mass spec shows parent.

EXAMPLE 14

21-(3-Carboxy-1-oxopropoxy)-17α-hydroxy-11α-(3,3-dimethyl-1-oxobutoxy)pregna-4-ene-3,20-dione The 17,21-acetonide of 11-epi-cortisol (15.00g, 0.0383) was dissolved in 50 ml of pyridine and reacted with 5.82 g (1.3 equiv) of t-butylacetyl chloride for 20 hours at room temperature under nitrogen. The mixture was partitioned between ether and aqueous sodium bicarbonate. The organic phase was washed with brine, dried over sodium sulfate and concentrated. The residue was chromatographed on silica gel (3% methanol in methylene chloride) to yield 21.47 g (100%) of product. This material was dissolved in dioxane. To this solution was added 10 ml of 10% aqueous HCl. The mixture was stirred for 3.25 hours. Another 10 ml of 10% HCl was added and the mixture was heated for 30 m at 50° C. The reaction was concentrated. The residue was partitioned between methylene chloride and aqueous sodium bicarbonate. The organic phase was dried over sodium sulfate and concentrated. The 18.45 g residue was dissolved in 30 ml of DMF and was reacted with 4.45 g of succinic anhydride and 100 mg of potassium bicarbonate at 46° C. for 40 minutes. Another 1 g of succinic anhydride was added and the reaction was stirred at room temperature for 4 hours. The reaction was concentrated. The residue was chromatographed on silica gel (4% methanol/.5% HOAc in methylene chloride) to yield 6.50 g of the hemisuccinate. This was dissolved in methanol and treated with 1 equivalent of sodium bicarbonate in water. The solution was lyophilized and the residue was crystallized from acetone and ether to yield a 4.25 g first crop. A second crop of 1.42 g was obtained. Anal. Calcd for $C_{30}H_{35}O_{10}Na \cdot H_2O$ (600.7). Calcd/Found: C, 61.98/57.95; H, 7.53/6.93; H20, 3.00/2.33. m/e+H+ =583. In another run, 6.44 g of the acetonide was converted to 1.00 g of the sodium hemisuccinate, decomp 186–226.

EXAMPLE 15

21-(3-Carboxy-1-oxopropoxy)-17α-hydroxy-11α-(2-phenyl-1-oxoethoxy)pregna-4-ene-3,20-dione, sodium salt The 17,21-acetonide of 11-epi-cortisol (6.00 g, 0.0149 mol) was dissolved in 25 ml of pyridine and reacted with 3.44 g (1.5 equiv) of phenylacetyl chloride for 20 hours at room temperature under nitrogen. Another 3 g of the acid chloride was added. After 4 hours, the mixture was partitioned between ether and aqueous sodium bicarbonate. The organic phase was washed with brine, dried over sodium sulfate and concentrated. The residue dissolved in 200 ml of acetone. To this solution was added 6 ml of 10% aqueous HCl. The mixture was stirred for 22 hours. The reaction was concentrated. The residue was partitioned between methylene chloride and aqueous sodium bicarbonate. The organic phase was dried over sodium sulfate and concentrated. The residue was chromatographed on silica gel (40/60 ethyl acetate/ hexane) to yield 4.81 g of a single spot material whose mass spec was consistent with the 21-OH, 11-ester. This material was dissolved in 25 ml of DMF and was reacted with 1.00 g of succinic anhydride and a trace of potassium bicarbonate at room temperature for 24 hours. Another 0.5 g of succinic anhydride was added and the mixture was stirred for 24 hours. The reaction was concentrated. The residue was chromatographed on silica gel (4% MeOH in methylene chloride to 4% methanol/.25% HOAc in methylene chloride) to yield 3.35 g of the hemisuccinate. This was dissolved in methanol and treated with 0.5 g of sodium bicarbonate in water. The solution was lyophilized and the residue was crystallized from acetone and ether to yield a 2/04 g first crop, decomp 130-134. Calcd for $C_{33}H_{41}O_9$·Na.H20 (620.7). Calcd/Found: C, 63.85/58.55; H, 6/67/6.52. m/e=603 (M.+H+).

EXAMPLE 16

21-(3-Carboxy-1-oxopropoxy)-17α-hydroxy-11α-[(2-furyl) oxomethoxy]pregna-4-ene-3,20-dione The 17,21-acetonide of 11-epi-cortisol (15.00 g, 0.0383) was dissolved in 50 ml of pyridine and reacted with 7.26 g (1.5 equiv) of furanoyl chloride for 20 hours at room temperature under nitrogen. The mixture was partitioned between ether and aqueous sodium bicarbonate. The organic phase was washed with brine, dried over sodium sulfate and concentrated. The residue was chromatographed on silica gel (3% methanol in methylene chloride) to yield 19.10 g (100%) of product. This material was dissolved in 200 ml of ethanol and 100 ml of dioxane and was treated with 10 ml of 10% aqueous HCl. After 3.5 hours at room temperature, another 10 ml of acid was added and the mixture was stirred at 50° C. for one hour The reaction was concentrated The residue was partitioned between methylene chloride and aqueous sodium bicarbonate. The organic phase was dried over sodium sulfate and concentrated. The 19.08 g of residue was dissolved in 30 ml of DMF and was reacted with 4.62 g of succinic anhydride and 100 mg of potassium bicarbonate at overnight. The reaction was concentrated. The residue was partitioned between 5% HCl and 1:1 ether/methylene chloride. The organic phase was washed with brine, dried over sodium sulfate and concentrated. This was crystallized from ethyl acetate to yield 10.53 g of the hemisuccinate (m/e=556, calcd for C30H36O10. Calcd/found: C, 64.74/63.69; H, 6.52/6.85.) A second crop of 4.00 g of the hemisuccinate was obtained. The first crop material was dissolved in methanol and treated with 1 equivalent (1.59 g) of sodium bicarbonate in water. The solution was lyophilized and the residue was crystallized from acetone and ether to yield a 9.80 g first crop. The second crop of 4.00 g was reacted with 500 mg of sodium carbonate to yield 3.19 g of the hemisuccinate sodium salt. Anal. Calcd for $C_{30}H_{33}O_{10}Na$·H20 (596.6). Calcd/Found: C, 60.40/59.34; H, 6.25/6.02; H20, 3.02/1.92. In another run, 7.51 g of the acetonide was converted to 0.98 g of the sodium hemisuccinate, decomp 242.

EXAMPLE 17

Bis-methylenedioxy protected 6α-methyl cortisone-3-ethylene-ketal

To a stirred suspension of 70 g (0.187 mol) 6α-methyl-cortisone in 650 ml CH2CL2, cooled to 0° C. in an ice/H20 bath, was added 110 ml concentrated HCl dropwise. To the stirred suspension was added 110 ml of 37% aqueous formaldehyde in 3 batches at one hour intervals after the cooling bath was removed. The reddish brown mixture was stirred for 18 hours at 25° C. The phases were separated, the aqueous phase was extracted with CH2Cl2, the combined organic phases were washed with H2O two times, saturated aqueous NaHCO3, dried (MgSO4) and the solvent removed in vacuo to leave 87.5 g of a brown foam. The material was chromatographed on 2 Kg silica gel, eluting with 1:1 hexane/ethyl acetate to give 25 g product and 6 g of a mixture of product and starting material. Rechromatographing the mixed fractions gave another 5 g of product; yield: 30 g (38%). The material was triturated with Et2O to give a white powder, mp=244°-248° C.

EXAMPLE 18

Bis-methylenedioxy protected 6α-methyl cortisone-3-ethyl-ene-ketal

A mixture of 20 g (48 mmol) of the compound of Example 17, 5.9 g (96 mmol) ethylene glycol, 300 ml benzene and 250 mg p toluene sulfonic acid was heated at reflux under N2 in a flask fitted with a Dean-Stark trap for 4 hours. The mixture was cooled to 25° C. and washed with 300 ml saturated NaHCO3. The organic phase was dried (MgSO4) and the solvent removed in vacuo to leave 22 g of an oil which crystallized from EtOAc to give 19.5 g (87%) of a white solid, mp=214°-216° C.

EXAMPLE 19

Bis-methylenedioxy protected 6α-methyl-11α-hydrocortisol, 3 ethylene ketal

To a solution of 20 g (43.5 mmol) of the compound of Example 18, 92 g (2 mol) absolute ethanol, 200 ml anhydrous Et2O and 500 ml dioxane (dried over a molecular sieve) in a 5L 3-neck flask fitted with mechanical stirrer and dewer condenser and cooled in a dry ice/acetone bath was distilled 3L of anhydrous ammonia. The cooling bath was removed and 15.4 g (2.2 mol) lithium wire was added piecewise over a 2 hour period. The NH3 was allowed to escape overnight. The flask was cooled to 0° C. and 1L ethyl acetate and 1L H2O was added with stirring until the solids dissolved. To the solution was added 200 ml saturated ammonium chloride. The phases were mixed and separated. The organic phase was dried (MgSO4) and the solvent removed in vacuo to leave 18.5 g of a solid. The material was triturated with Et2O to give 15.5 g (78%) of a white powder, mp=247°-250° C. An analytical sample was crystallized from acetone, mp=250°-252° C.

EXAMPLE 20

Bis-methylenedioxy protected 6α-methyl-11α-hydrocortisol

A solution of 57 g (0.123 mol) of the compound of Example 19, 4 g p-toluene sulfonic acid and 3L acetone was stirred at 25° C. for 24 hours. The acetone was removed in vacuo. The residue dissolved in 2L of CH2Cl2 and washed with 1L H2O and 1L saturated NaHCO3. The organic phase was dried (MgSO4) and the solvent removed in vacuo to leave 52 g of a green foam. The material was flash chromatographed in 3 batches on silica gel (about 200 g) eluting with 1:1 hexane/ethyl acetate to give 20 g (40%) of the title product. A sample of the title compound was crystallized from ethyl acetate, mp=203°-204° C.

EXAMPLE 21

11α,17,21-Trihydroxy-6α-methyl-pregn-1,4-diene-3,20-dione, 17,20,21-bis-methylenedioxy A mixture of 7.5 g (18 mmol) of the compound of Example 20, 6.13 g (27 mmol) 2,3-dichloro-5,6-dicyanobenzoquinone and 80 ml dioxane (dried over a molecular sieve) was heated at reflux for 18 hours. The mixture was cooled to 25° C. and filtered. The filtrate (black) was flash chromatographed on silica gel (about 200 g), eluting with 1:1 hexane/ethyl acetate to give 6.2 g (83%) of the title compound as a yellow powder after crystallizing from hexane/ethyl acetate, mp=255°–258° C.

EXAMPLE 22

11α,17α,21-Trihydroxy-6α-methyl-pregn-4-ene-3,20-dione

A mixture of 3 g (7.18 mmol) of the compound of Example 20, and 30 ml of 88% formic acid was heated on a steam bath for 30 minutes. The mixture was cooled to 0° C. and neutralized with 60 ml 45% KOH. The mixture was distributed between 100 ml $H_2O$ and 150 ml $CH_2C_2$. The aqueous phase was extracted 2 times with 100 ml $CH_2Cl_2$. The combined organic phases were dried (MgS04) and the solvent removed in vacuo to leave 3 g of a brown foam. The resultant formates were hydrolized by stirring the material with 100 ml methanol and 20 ml of 10% $K_2CO_3$ at 25° C. for 30 minutes. The mixture was acidified with 6 ml acetic acid. The methanol was removed in vacuo, the residue taken up in $CH_2Cl_2$ (100 ml), washed with $H_2O$ (100 ml), dried (MgSO4) and the solvent removed in vacuo to leave 2.5 g of a brown foam. The material was chromatographed on silica gel (175 g) eluting with 3% methanol, 97% ethyl acetate to give 1.08 g of the title compound as a white foam. An analytical sample was crystallized from ethyl acetate, mp=203°–206° C.

EXAMPLE 23

11α,17α,21-Trihydroxy-6α-methyl-pregn-1,4-diene-3,20-dione

A mixture of 2.0 g (4.8 mmol) of the compound of Example 21 and 20 ml 60% formic acid was heated at 100° C. for one hour. The mixture was cooled to 25° C., diluted with 100 ml ethyl acetate and 75 ml $H_2O$ and neutralized with 30 ml 45% KOH. The phases were mixed and separated. The aqueous solution was extracted with ethyl acetate, the combined organic phases were dried (MgSO4) and the solvent removed in vacuo to leave 2 g of a brown foam. The material was stirred with 20 ml methanol and 8 ml 10% aqueous $K_2CO_3$ at 25% for 3 minutes. The methanol was removed in vacuo and the residue distributed between $H_2Cl_2$ (75 ml) and $H_2O$ (75 ml). The aqueous solution was extracted with $CH_2Cl_2$, the combined organic phases were dried (MgSO4) and the solvent removed in vacuo to leave 1.79 g of a glossy solid which was triturated with $Et_2O$ to give 1.5g of the title compound as a light yellow powder (83%).

EXAMPLE 24

11α-Hydroxy-21-(3-carboxy-1-oxapropoxy)-17-hydroxy-6α-methyl-pregn-1,4-diene-3,20-dione, sodium salt, hemihydrate A mixture of 1.5 g (4.01 mmol) of the compound of Example 23, 0.66 g (6.6 mmol) succinic anhydride and 15 ml pyridine was stirred at 25° C. for 24 hours. The mixture was added dropwise to 150 ml ice cold 10% HCl. The solids were collected on a buchner funnel, washed with cold $H_2O$ and dried in vacuo to leave 1 g of a light yellow solid (53%). Mass spec: (E.I>) m/e=474 (m+); 135 (base peak).

To 0.4 g (0.84 mmol) of the above material in 5 ml methanol was added 0.071 g (0.84 mmol)NaHCO3 in 1 ml $H_2O$. The mixture was stirred at 25° C. for one hour and the solvents removed in vacuo to leave a pale yellow solid. The material was triturated with acetone to give 0.35 g (85%) of a pale yellow solid, mp=310° (dec.).

EXAMPLE 25

11α,17,21-Trihydroxy-6α-methyl-pregn-1,4-diene-3,20-dione,17,21-acetonide

A mixture of 4.8 g (12.8 mmol) of the compound of Example 23, 75 ml of 2.2-dimethoxypropane. 30 ml dimethylformamide and 0.12 g p-toluenesulfonic acid was refluxed for 3 hours. The mixture was cooled to 25° C. and distributed between 300 ml ethyl acetate, 150 ml $H_2O$ and 150 ml saturated NaHCO3. The organic phase was dried (MgS04) and the solvent removed in vacuo to leave 7.2 g crude product as a brown oil. The material was chromatographed on silica gel (175 g) eluting with 1,1 hexane/ethyl acetate to give 2.73 g (52%) of the title compound as a white foam. An analytical sample was crystallized from hexane/ethyl acetate to give a white powder, mp=185°–187° C.

EXAMPLE 26

11α-Acetoxy-17αa,21-acetonide-6α-methyl-pregn-1,4-diene-3,20-dione

A mixture of 1.0 g (2.4 mmol) of the compound of Example 25, 5 ml acetic anhydride and 20 ml pyridine was stirred at 25° C. for 18 hours. The pyridine was removed in vacuo and the residue distributed between 100 ml ice cold 10% HCl and 100 ml ethyl acetate. The organic phase was dried (MgSO4) and the solvent removed in vacuo to leave 2 g of an oil. The material was chromatographed on silica gel (175 g) eluting with 70% hexane, 30% ethyl acetate to give 1.0 g of a white foam.

EXAMPLE 27

11α-Acetoxy-17αc,21-dihydroxy-6α-methyl-pregn-1,4-diene-3,20-dione A mixture of 1.0 g (2.2 mmol) of the compound of Example 26, 15 ml acetone, 2 ml $H_2O$ and 20 drops of 10% HCl was heated at 45° C. for 3 hours. The mixture was cooled to 25° C. overnight. The solids were collected and washed with cold acetone to leave 0.51 g of the title compound as a white powder. The filtrate was distributed between ml $CH_2Cl_2$ and 35 ml $H_2O$. The organic phase was dried (MgSO4) and the solvent removed in vacuo to leave another 0.23 g of the title compound after $Et_2O$ trituration, mp=275° (dec.).

EXAMPLE 28

11α-Acetoxy-21-(3-carboxy-1-oxopropoxy)-17α-hydroxy-6α-methyl-pregn-1,4-diene-3.20-dione, sodium salt, hemihydrate The 21-succinate was prepared as in Example 24 using 0.74 g (1.8 mmol) of the compound of Example 27, 0.36 g (3.6 mmol) succinic anhydride and 10 ml pyridine to give 0.88 g (96%) of the succinate derivative.

The sodium salt was prepared as in Example 24 using 0.8 g of the above succinate steroid, 0.13 g (1.55 mmol) NaHCO3, 2 ml $H_2O$ and ml methanol to give 0.82 g (85%) of the title compound after $Et_2O$ trituration, mp=325° (dec.). Mass spec: (F.A.B ) m/e=539 (m+=H). Anal. calcd for $C_{28}H_{35}O_9Na.2.5\ H_2O$ C, 57.62; H, 6.91. Found: C, 57.34; H, 6.05.

EXAMPLE 29

11α-Benzoyl-17,21-acetonide-6α-methyl-pregn-1,4-diene-3,20-dione

A mixture of 1.0 g (2.4 mmol) of the compound of Example 25, ml pyridine and 0.37 g (2.65 mmol) benzoylchloride was stirred at 25° C. for 24 hours. The mixture was distributed between 250 ml ice cold 10% HCl and 250 ml ethyl acetate. The organic phase was washed with saturated NaHCO$_3$, dried (MgSO4) and the solvent removed in vacuo to leave 1.4 g of an oil which crystallized from hexane/ethyl acetate to give 0.7 g of the title compound, mp=122°–125° C. Another 0.3 g of the compound of Example 28 was isolated after chromatography of the mother liquors on silica gel, eluting with 70% hexane/30% ethyl acetate: yield=81%.

EXAMPLE 30

11α-Benzoate-17α,21-dihydroxy-6α-methyl-pregn-1,4-diene-3,20-dione

A mixture of 1 g (1.93 mmol) of the compound of Example 29, 15 ml acetone, 2 ml H$_2$O and 1 ml 10% HCl was heated on a steam bath for 30 minutes. The mixture was allowed to cool and distributed between CH$_2$Cl$_2$ (100 ml) and saturated NaHCO$_3$ (75 ml). The organic phase was dried (MgSO4) and the solvent removed in vacuo to leave 1 g of a yellow solid which was recrystallized from CH$_2$Cl$_2$ to give 0.57 first crop, mp=141°–143..5° C.) and 0.4 g second crop (total yield 100%) of the title compound.

EXAMPLE 31

11α-Benzoate-21-(3-carboxy-1-oxapropoxy)-17α-hydroxy-6α-methyl-pregn-1,4-diene-3,20-dione, sodium salt The 21-succinate was prepared as in Example 24 using 0.9 g (1.9 mmol) of the compound of Example 30, 0.38 g (3.76 mmol) succinic anhydride and 20 ml pyridine to give 0.8 g of the succinate derivative.

The sodium salt was prepared as in Example 24 using 0.65 g of the above 21-succinate, 5 ml methanol, 94 mg (1.12 mmol) NaHCO$_3$ and 2 ml H$_2$O to give 0.7 g of a pale white lyophilized powder, mp=242° (dec.).

EXAMPLE 32

11α,17α,21-Trihydroxy-21-(3-carboxy-1-oxopropoxy)-6α-methyl-pregn-4-ene-3,20-dione, sodium salt A mixture of 0.5 g (1.33 mmol) of the compound of Example 22, 0.13 g (1.33 mmol) succinic anhydride, 4 ml CH$_2$Cl$_2$, 0.13 g (1.3 mmol) triethyl amine and 5 mg 4-dimethylaminopyridine was stirred at 25° C. for 18 hours. Another 50 mg succinic anhydride was added and the mixture stirred another 24 hours at 25° C. The mixture was diluted with 20 ml CH$_2$Cl$_2$ and washed with 10 ml 5% HCl. The organic phase was dried (MgSO4) and the solvent removed in vacuo to leave a brown oil. The material was chromatographed on silica gel, eluting with 0.1% acetic acid, 1.9% methanol and 98% ethyl acetate to give 0.35 g of 21-succinate plus 0.22 g of material containing less polar impurities. $^1$H NMR (80 mHz, CDCl$_3$): δ=5.80 (m, 1H, H-C4); 5.05, 5.0 (d, 2H, Hz-C21); 1.33 (S, 3H, H$_z$-C19); 1.13, 1.05 (d, 3H, HzC-C6); 0.71 (S, 3H, Hz-C18).

The sodium salt was formed as in Example 24 using 29 mg NaHCO$_3$, 0.5 ml H$_2$O and 2 ml methanol to give 300 mg of the title compound as a dihydrate, mp=320° (dec.).

EXAMPLE 33

N-Methyltaurine amide of 17α-hydroxypregna-1,4,9(11)-triene-6α-fluoro-3,20-dione-21-hemisuberate, sodium salt Pivaloyl chloride (8.76 g, 0.073 mol) was reacted in 350 ml of pyridine with 34.22 g (0.109 mol) of 8-oxo-[(2-sulfoethyl)methylamino]oxtanoic acid, monosodium salt. A 13.15 g (0.0363 g) sample of 6α-fluoro-21-hydroxy-17α-hydroxy-pregna-1,4,9(11)-trien-3,20-dione was added after 2 hours. The mixture was stirred for 7 days. The mixture was concentrated and partitioned between n-butanol and aqueous sodium sulfate. The organic phase was dried over sodium sulfate and concentrated. The residue was chromatographed on silica gel (2% methanol/methylene chloride to 15%). The product was dissolved in methylene chloride and n-butanol and was washed with sodium sulfate in water. The organic phase was dried and concentrated. The residue was triturated with ether to yield 14.56 g of product which foamed at 130° C. HPLC analysis on C-18 showed 92% purity. Anal. Calcd for C$_{33}$H$_{45}$NFSNaO$_9$. Calcd/Found: C, 58.83/58.11; H, 6.73/7.01; N, 2.08/2.17.

EXAMPLE 34

21-(3-Carboxy-1-oxopropoxy)-17α-hydroxy-11α-(phenyloxo methoxy)-pregna-4-ene-3,20-dione, sodium salt A 5.00 g (.0132 mol) sample of the BMD protected 11-epi-cortisol was reacted in 60 ml of pyridine with 5.56 g (3 equiv) of benzoyl chloride for 25 hours. The mixture was concentrated and the residue was partitioned between methylene chloride and aqueous sodium bicarbonate. The organic phase was dried over sodium sulfate and concentrated. The residue was chromatographed on silica gel (methylene chloride to 2% methanol/methylene chloride) to yield 5.6 g of the 11-O-benzoate. This material was stirred at 45° C. in formic acid for 4 hours. The reaction was concentrated and the residue was stirred with methanol, water and potassium carbonate for 3 minutes. This removed the formate esters. This mixture was partitioned between methylene chloride and water. The organic phase was dried and concentrated. The residue was chromatographed on silica gel (25% ethyl acetate/hexane to 60%) to yield 2.25 g of a white solid product and 1.28 g of bismethylenedioxy protected starting material. This 1.28 g was recycled to yield 810mg of the 21-hydroxy steroid. The 2.25 g sample was dissolved in 10 ml of DMF and was reacted with 0.60 g of succinic anhydride at 50 degrees for 4 hours. The reaction was partitioned between ethyl acetate and water and dried over magnesium sulfate. The product was chromatographed on RP2 silica gel (40% ethyl acetate/hexane to 100%) to yield 1.90 g of pure product. This material was converted to the sodium salt with sodium bicarbonate (83 mg). The product was triturated with ethyl acetate and ether to yield 1.87 g of product, mp>270. Anal. Calcd for C$_{32}$H$_{35}$O$_9$Na·2H$_2$O. Calcd/Found: C,61.73/59.57; H, 6.31/6.26.

EXAMPLE 35

21-(3-Carboxy-1-oxopropoxy)-17α-hydroxy-11α-hydroxypregna-4-ene-3,20-dione

A solution of 3.60 g of 11-epi-cortisol and 1.00 g of succinic anhydride in 45 ml of pyridine was stirred for 4 days at room temperatures The reaction was concentrated. The residue was partitioned between methylene chloride and water. The organic phase was partitioned with sodium bicarbonate. The aqueous layer was washed with methylene chloride. The aqueous layer was acidified with 10% aqueous U HCl and was extracted with chloroform. The organic phase was concentrated. The residue was chromatographed on RP2 silica gel (20% ethyl acetate/methylene chloride) to yield the product which was crystallized from hot ethyl acetate to yield 2.00 g of the white, solid product, mp 208–209. Anal. Calcd for $C_{25}H_{34}O_8$. Calcd/Found: C, 64.92/64.24; H, 7.41/7.08

EXAMPLE 36

N-Methyltaurine amide of 17α-hydroxypregna-1,4,9(11)triene-6α-fluoro-16β-methyl-3,20-dione-21-hemisuberate, sodium salt A mixture of 41.06g (.131 mol) of 8-oxo-[(2-sulfoethyl)methylamino]octanoic acid, monosodium salt, and 10.49 g (.087 mol) of pivaloyl chloride were stirred in 400 ml of pyridine for 2.5 h. A 15.78 g (0.0436 mol) sample of 21-hydroxy-16β-methyl-6α-fluoro-pregn-1,4,9(11)triene was added and the reaction was stirred for 20 hours. The mixture was concentrated and partitioned between n-butanol, water, sodium sulfate and sodium bicarbonate (0.087 mol). The organic phase was dried over sodium sulfate and concentrated. The residue was chromatographed on silica gel (2% methanol/methylene chloride to 12%) to yield, after triturating to a white solid with ether, a 20.58 g pure cut whose mass spec was consistent with the product, mp to a glass 110–114. Anal. Calcd for $C_{32}H_{43}NFSO_9Na$-.5$H_2O$. Calcd/Found: C, 57.47/55.88; H,6.63/6/74; N, 2.09/2.90; H2O1.35/.97.

EXAMPLE 37

A 16.23g (0.0517 mol) sample of 8-oxo-[(2-sulfoethyl)methylamino]octanoic acid, monosodium salt, and 4.99 g (.0414 mol) of pivaloyl chloride in 120 ml of pyridine was stirred in an ice bath for 3.5 hours. 21-Hydroxy-6α-fluoro-pregna-1,4,9(11),16-tetraene (6.70 g (0.0207 mol) was added. The mixture was stirred for 19 hours and was then concentrated. The residue was poured into water which was saturated with sodium sulfate. Carbon dioxide was bubbled into the solution. The acidified mixture was partitioned between n-butanol and aqueous sodium sulfate. The organic phase was dried for 2h over magnesium sulfate. The product was chromatographed on silica gel (5% methanol/methylene chloride to 10% with 1% acetic acid) to yield, after ether trituration, 5.72 g of a tacky solid. This material was treated with 0.76 g of sodium bicarbonate in the usual way. The sodium salt was triturated with acetonitrile and ether to yield 4.24 g of product, mp 218–220. Anal. Calcd for $C_{32}H_{41}NO_8FSNa$-.8$H_2O$. Calcd/Found: C,58.58/5.56; H, 6.54/6.10; N,2.13/1.97; H2O,2.20/1.97.

EXAMPLE 38

21-(3-Carboxy-1-oxopropoxy)-17α-hydroxy-11α-methoxypregna-4-ene-3,20-dione (a) A stirred mixture of 2.0 g (4.4 mmol) steroid bis-methylenedioxy ketal protected 11-epi-cortisone, 60 ml of THF (dried over a molecular sieve) and 1.06 g (22 mmol) sodium hydride as a 50% mineral oil dispersion (freed from mineral oil by washing with hexane 2 times) was heated at 65° C. for 2 hours. The mixture was allowed to cool to 25° C. and 2.75 ml (6.25 g, 44 mmol) of methyl iodide was added via syringe in a steady stream. The mixture was again heated with stirring at 65° C. for 4 hours. The mixture was cooled to 0° C. in an ice/H2O bath and quenched with 50 ml H2O added dropwise. The mixture was extracted 2 times with 150 ml ethyl actate. The combined extracts were dried (MgSO4) and the solvent removed in vacuo to leave 2.04 g (100%) of a white solid, one spot by ILC. An analytical sample was crystallized from hexane/ethyl acetate, mp=189–190.

(b) A mixture of 3.0 g (6.5 mmol) of the product from 38(a) and 40 ml of 88% aqueous formic acid was warmed on a steam bath with stirring for 30 minutes. The mixture was diluted with 40 ml methanol, cooled to 0° C. in an ice/H2O bath and neutralized with 80 ml of 50% NaOH added dropwise. The mixture was diluted with 50 ml H2O and extracted 3 times with 100 ml CH2Cl2. The combined extracts were dried (MgSO4) and the solvent removed in vacuo to leave 2.8 g of a foam. The material was dissolved in 90 ml methanol and 30 ml of 10% aqueous K2CO3 was added. The mixture was stirred at 25° C. for 18 hours, acidified with 3 ml acetic acid and concentrated in vacuo. The residue was distributed between 150 ml H2O and 150 ml CH2Cl2. The aqueous phase was extracted with 100 ml CH2Cl2. The combined CH2Cl2 solutions were dried (MgSO4) and the solvent removed in vacuo to leave 1.24 g of a yellow foam. The material was chromatographed on silica gel, eluting with 2% methanol/98% CH2Cl2 to give 0.29 g (12%) of compound.

(c) A mixture of 0.28 g (0.74 mmol) of the compound from 38(b), 0.3 g (3.0 mmol) succinic anhydride and 5 ml pyridine was stirred at 25° C. for 48 hours. The mixture was added dropwise to 60 ml of ice cold 10% HCl with stirring. The precipitate was collected and lyophilized to 0.3 g of the title compound and white powder. $^1$H NMR (80 mHz, CDCl3, CD3OD: δ=5.73 (S, 1H, H-C4); 5.04, 4.97 (d, 2H, H2-C21); 3.75–3.95 (m, 1H, CH-C11); 3.29 (S, 3H, OCH3); 2.75 (S, 4H, succinate-CH2-); 2.7–1.0 (m, ring-CH2-), 1.26 (S, 3H, H3-C19); 0.72 (S, 3H, H3-C18).

EXAMPLE 39

21-(3-Carboxy-1-oxopropoxy)-17Aα-hydroxy-11α-ethoxypregna-4-ene-3,20-dione (a) A mixture of bis-methylenedioxy ketal protected 11-epi-cortisol, 3.0 g (6.7 mmol), 1.86 (38.8 mmol) of 50% sodium hydroxide, 90 ml THF and 15 ml (21.9 g, 0.2 mmol) bromoethane was heated at 50° C. for 56 hours after bromoethane addition. The reaction was worked up as in Example 38(a) and chromatographed on silica gel, eluting with 70% hexane/30% ethyl acetate gave 1.94 (60%) of the α-11-O ethyl ether. An analytical sample was triturated with diethyl ether, mp=152°–154° C.

(b) A mixture of 1.9 g (3.96 mmol) of the product of 39(a) and 20 ml of 88% aqueous formic acid was warmed on a steam bath with stirring for 30 minutes. The mixture was concentrated in vacuo and the residue distributed between 75 ml CH$_2$Cl$_2$ and 75 ml saturated aqueous NaHCO$_3$. The organic phase was dried (MgSO4) and the solvent removed in vacuo to leave 1.47 g of a brown foam. The material was stirred with 50 ml methanol and 20 ml 10% aqueous potassium carbonate for 18 hours. The mixture was acidified with 3 ml acetic acid, concentrated in vacuo and the residue distributed between 75 ml CH$_2$Cl$_2$ and 75 ml H$_2$O. The aqueous phase was extracted 3 times with 50 ml CH$_2$Cl$_2$. The combined organic phases were washed with saturated aqueous NaHCO$_3$, dried (MgSO4) and the solvent removed in vacuo to leave 1.4 g of crude product. The material was chromatographed on silica gel, eluting with 2% methanol and 98% CH$_2$Cl$_2$ to give 0.49 g (33%) of product as a white foam.

(c) Following the procedure of Example 38(c) only substituting 0.45 g (1.15 mmol) of the product of Example 39(b) for the compound of Example 38(b) and using 0.42 g (4.2 mmol) of succinic anhydride and 10 ml of pyridine gave 0.13 g of the title compound.

EXAMPLE 40

21-(3-Carboxy-1-oxopropoxy)-17α-hydroxy-11α-phenylmethyloxy-pregna-4-ene-3,20-dione (a) A mixture of 3.0 g (6.7 mmol) bis methylenehydroxy ketal protected 11-epi-cortisol, 30 ml of benzyl chloride, 15 ml of 50% sodium hydroxide and 0.3 g of tetra-N-butylammonium hydrogen sulfate was stirred at 25° C. for 7 days. The mixture was diluted with 50 ml H$_2$O and extracted with 150 ml Cah$_2$Cl$_2$ twice. The combined extracts were dried (MgSO$_4$), the solvent removed in vacuo and the residue chromatographed on silica gel, eluting with 1L of 9:1 hexane/ethyl acetate followed by 2.3:1 hexane/ethyl acetate to give 3.5 g (97%) of a white powder. An analytical sample was crystallized from hexane/ethyl acetate to give a material with mp=194°–197° C.

(b) The hydrolysis was carried out as in Example 39(b) using 3.0 g (5.6 mmol) of the compound from 40(a) above and 30 ml of 88% formic acid. The reaction was worked up as in Example 39(b) with the chromatography on silica gel eluting with 2% methanol, 98% ethyl acetate to give 0.9 g (36%) of 11α-phenylmethoxy cortisol as a white foam. After trituration with diethyl ether the mp=151°–155° C.

(c) Procedure carried out as in Example 38(c) using 0.8 g (1.77 mmol) of the compound from 40(b), 0.71 g (7.1 mmol) succinic anhydride and 10 m,l pyridine to give 0.8 g of the title compound as a pale white powder. $^1$H NMR (80 mHz, CDCl$_3$); δ=7.30 (S,5H, aromatic-H); 5.70 (S, 1H, H-C4); 5.0, 4.9 (d,,12H, H$_2$-C21); 4.55, 4.44 (d,2H, benzylic); 2.73 (S, 4H, succinate-CH2 s); 2.4–1.0 (m, ring-CH2,s); 1.21 (S, 3H, H$_3$-C19); 0.70 (S, 3H, H$_3$-C18).

EXAMPLE 41

| | |
|---|---|
| 21-(3-Carboxy-1-oxopropoxy)-17α-hydroxy-6α-methylpregna-1,4,9(11)-triene-3,20-dione | 155 mg |
| Dilute NaOH to adjust pH to 5.3 | |
| Sterile water for injection to make 1 mlr | |

EXAMPLE 42

| | |
|---|---|
| 21-(3-Carboxy-1-oxopropoxy)-17α-hydroxy-6α-methylpregna-1,4,9(11)-triene-3,20-dione | 153 mg |
| Adipic acid | 7.3 mg |
| Methyl paraben | 1.5 mg |
| Propyl paraben | 0.2 mg |
| NaOH (dilute) to adjust pH to 5.4 | |
| Sterile water for injection to make 1 ml | |

EXAMPLE 43

| | |
|---|---|
| 21-(3-Carboxy-1-oxopropoxy)-17α-hydroxy-6α-methylpregna-1,4,9(11)-triene-3,20-dione | 166 mg |
| Creatine | 8.0 mg |
| Acetic acid | 4.6 mg |
| Sodium acetate | 2.0 mg |
| Sodium bisulfite | 1.0 mg |
| Disodium edetate | 0.5 mg |
| Benzyl alcohol | 8.8 mg |
| HCl (dilute) or NaOH (dilute) to adjust pH to 5.0 | |
| Water for injection to make 1 ml | |

FORMULA CHART

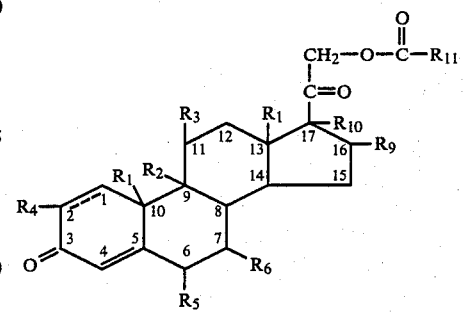

Formula I

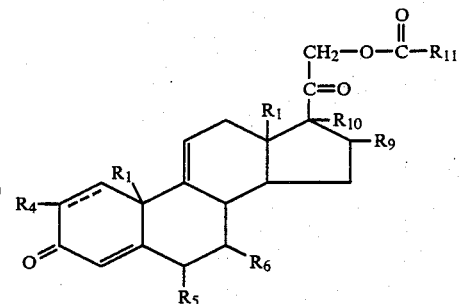

Formula II

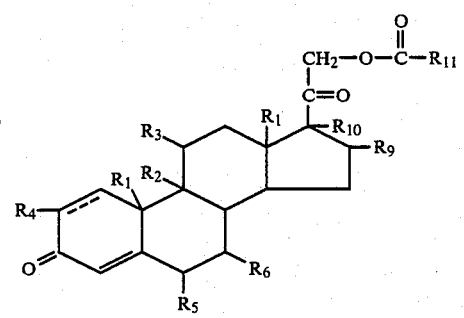

Formula III

FORMULA CHART
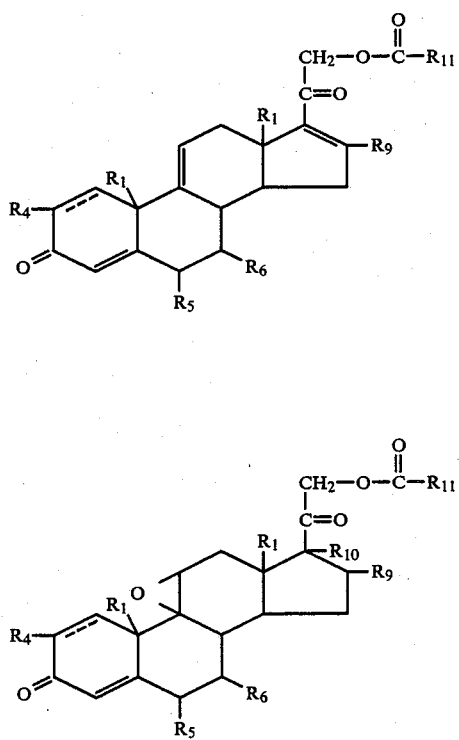
Formula IV
Formula V
-continued
FORMULA CHART
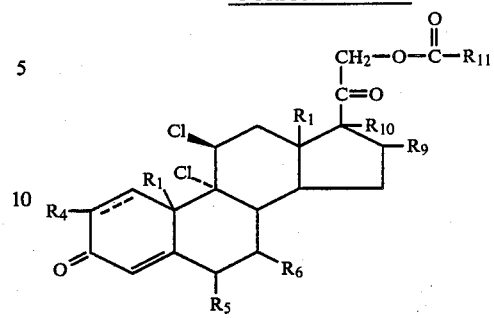
Formula VI
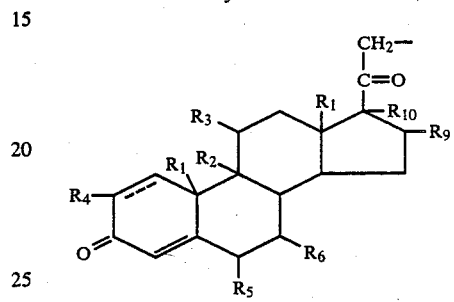
Formula VII
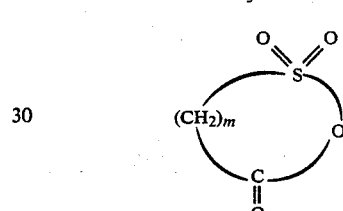
Formula A
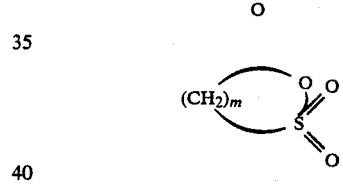
Formula B
We claim:
1. 21-(3-Carboxy-1-oxopropoxy)-17α-hydroxy-11α-(3,3-dimethyl-1-oxobutoxy)pregna-1,4-diene-3,20-diene and pharmaceutically acceptable salts thereof.
2. A compound according to claim 1 which is 21-(3-Carboxy-1-oxopropoxy)-17α-hydroxy-11α-(3,3-dimethyl-1-oxobutoxy)pregna-1,4-diene-3,20-diene sodium salt.
* * * * *